US011946934B2

(12) United States Patent
Jin et al.

(10) Patent No.: US 11,946,934 B2
(45) Date of Patent: Apr. 2, 2024

(54) BIOMARKER FOR PREDICTING THE SENSITIVITY TO A PROTEIN KINASE INHIBITOR AND A USE THEREOF

(71) Applicant: Wellmarker Bio Co., LTD., Seoul (KR)

(72) Inventors: Dong Hoon Jin, Seoul (KR); Seung Woo Hong, Seoul (KR); Jai Hee Moon, Seoul (KR); Jae Sik Shin, Seoul (KR)

(73) Assignee: Wellmarker Bio Co., LTD., Seoul (KR)

( * ) Notice: Subject to any disclaimer, the term of this patent is extended or adjusted under 35 U.S.C. 154(b) by 991 days.

(21) Appl. No.: 15/508,870

(22) PCT Filed: Sep. 3, 2015

(86) PCT No.: PCT/KR2015/009322
§ 371 (c)(1),
(2) Date: Mar. 19, 2018

(87) PCT Pub. No.: WO2016/036172
PCT Pub. Date: Mar. 10, 2016

(65) Prior Publication Data
US 2018/0180616 A1 Jun. 28, 2018

(30) Foreign Application Priority Data
Sep. 3, 2014 (KR) .................. 10-2014-0116787

(51) Int. Cl.
| *C12Q 1/68* | (2018.01) |
| *C12Q 1/6886* | (2018.01) |
| *G01N 33/50* | (2006.01) |
| *G01N 33/53* | (2006.01) |
| *G01N 33/574* | (2006.01) |
| *G01N 33/68* | (2006.01) |

(52) U.S. Cl.
CPC ......... *G01N 33/574* (2013.01); *C12Q 1/6886* (2013.01); *G01N 33/5011* (2013.01); *G01N 33/53* (2013.01); *G01N 33/57484* (2013.01); *G01N 33/6893* (2013.01); *C12Q 2600/106* (2013.01); *C12Q 2600/156* (2013.01); *C12Q 2600/158* (2013.01); *G01N 2800/52* (2013.01)

(58) Field of Classification Search
None
See application file for complete search history.

(56) References Cited

U.S. PATENT DOCUMENTS
2008/0113874 A1 5/2008 Bunn et al.

FOREIGN PATENT DOCUMENTS

| KR | 10-2012-0100845 A1 | 9/2012 |
| KR | 10-1350006 B1 | 1/2014 |
| WO | WO 2008-066498 A1 | 6/2008 |
| WO | WO 2009-051992 A1 | 4/2009 |
| WO | WO 2016-018087 A1 | 2/2016 |

OTHER PUBLICATIONS

Yan et al; Invest New Drugs, vol. 31, pp. 833-844, 2013.*
Valle et al; Lancet Oncol, 2021; vol. 22, pp. 1468-1462.*
Rimassa et al; Lancet Oncol, 2018; vol. 19, pp. 682-293.*
Genbank: CAA49634.1, "Tyrosine kinase [*Homo sapiens*]," Apr. 18, 2005, two pages.
Myers et al., "Detection of single base substitutions in total genomic DNA," Nature 313: 495-498, Feb. 7, 1985.
NCBI, NCBI Reference Sequence: XM_005265170.2, "Predicted: *Homo sapiens* macrophage stimulating 1 receptor (c-met-related tyrosine kinase) (MST1R), transcript variant X1, mRNA," Feb. 3, 2014, three pages.
Wang et al., "RON confers lapatinib resistance in HER2-positive breast cancer cells," Cancer Letters 340: 43-50, 2013.
Zhou et al., "Altered expression of the RON receptor tyrosine kinase in primary human colorectal adenocarcinomas: generation of different splicing RON variants and their oncogenic potential," Oncogene 22: 186-197, 2003.
Zou et al., "Sensitivity of Selected HumanTumor Models to PF-04217903, a Novel Selective c-Met Kinase Inhibitor," Molecular Cancer Therapeutics 11(4): 1036-1047, 2012.
Danilkovitch-Miagkova, et al., "Oncogenic Mutants of RON and MET Receptor Tyrosine Kinases Cause Acivation of the β-Catenim Pathway" *Molecular and Cellular Biology* 21(17):5857-5868, Sep. 2001.
Yoon, et al., "Expression of the receptor tyrosine kinase recepteur d'origine nantais and its association with tumor progression in hypopharyngeal cancer," Head & Neck (2013) vol. 35(8):1106-1113, 8 pages.
Dussault and Bellon, "From Concept to Reality, The Long Road to c-Met and RON Receptor Tyrosine Kinase Inhibitors for the Treatment of Cancer," Anti-Cancer Agents in Medicinal Chemistry 9:221-229 (2009).

* cited by examiner

*Primary Examiner* — Jehanne S Sitton
(74) *Attorney, Agent, or Firm* — Cooley LLP

(57) ABSTRACT

The present disclosure relates to a biomarker for predicting the sensitivity to a protein kinase inhibitor and a use thereof. The present disclosure provides a marker, a composition, and a kit for predicting the sensitivity to a protein kinase inhibitor, and a prediction method thereof. According to the present disclosure, the marker has an excellent effect of predicting the sensitivity to a protein kinase inhibitor, and thus the present disclosure can be useful for cancer treatment.

3 Claims, 26 Drawing Sheets

Specification includes a Sequence Listing.

[Fig. 1a]
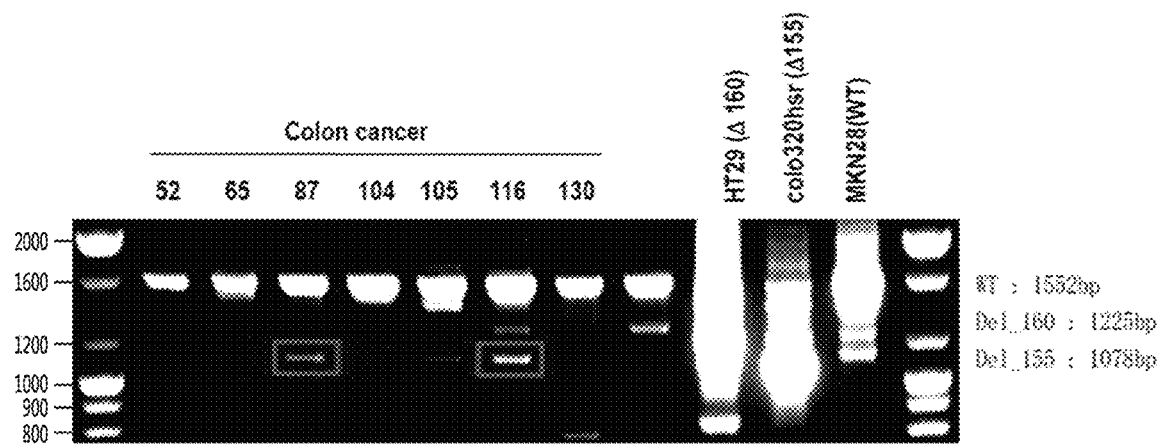
[Fig. 1b]
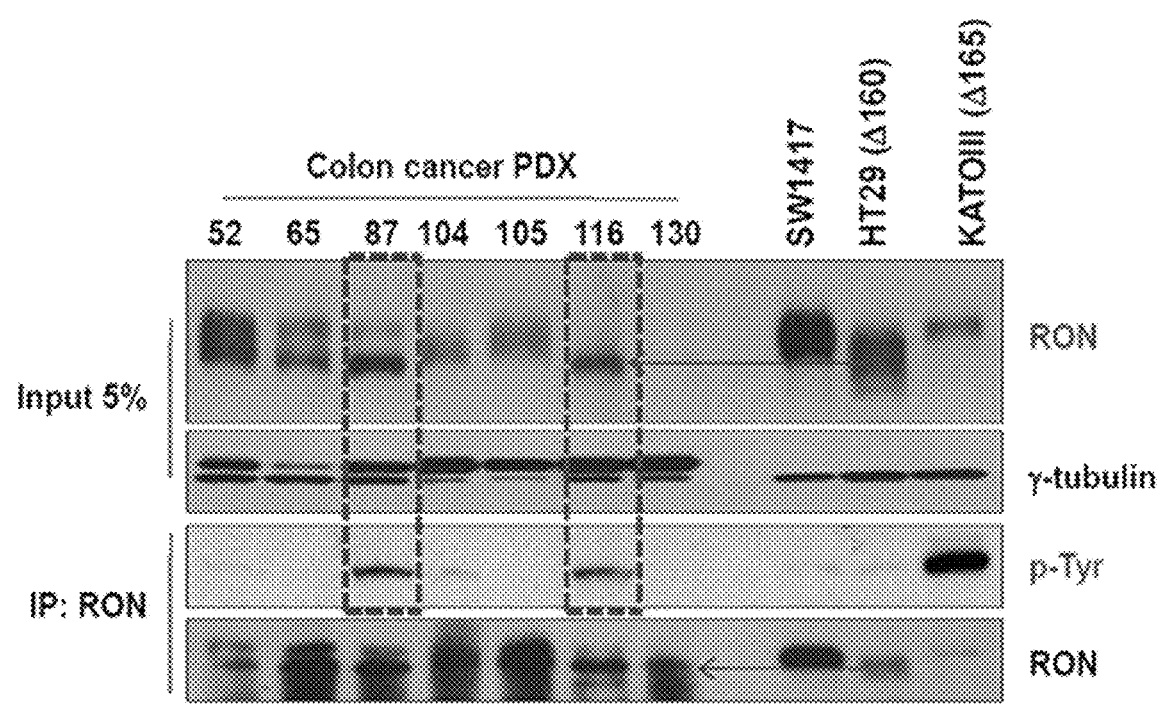

[Fig. 1c]
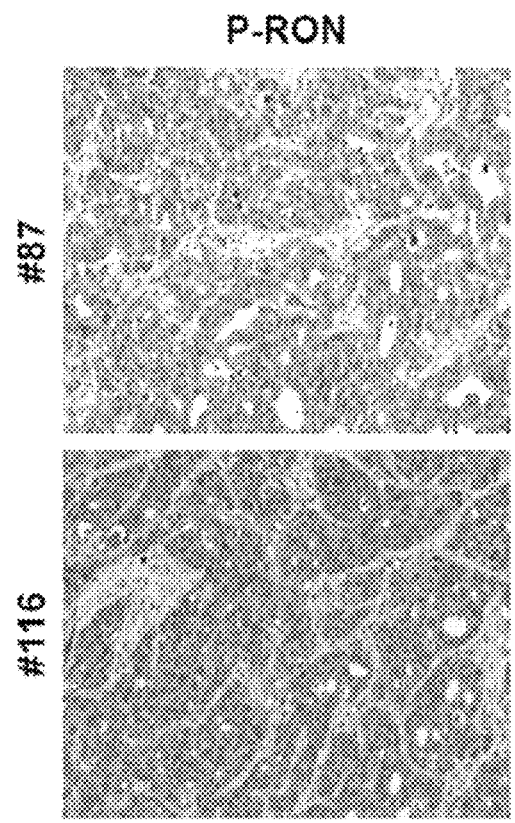

[Fig. 2a]
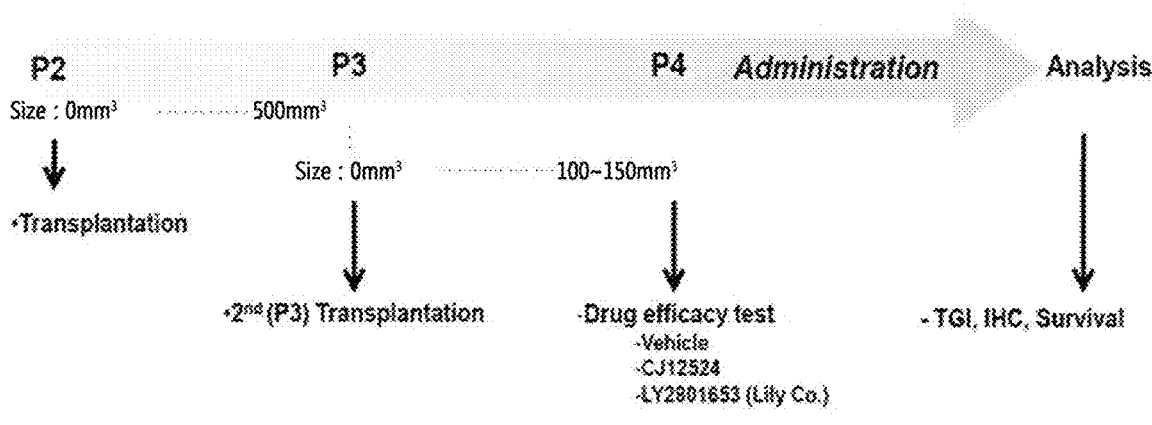

[Fig. 2b]
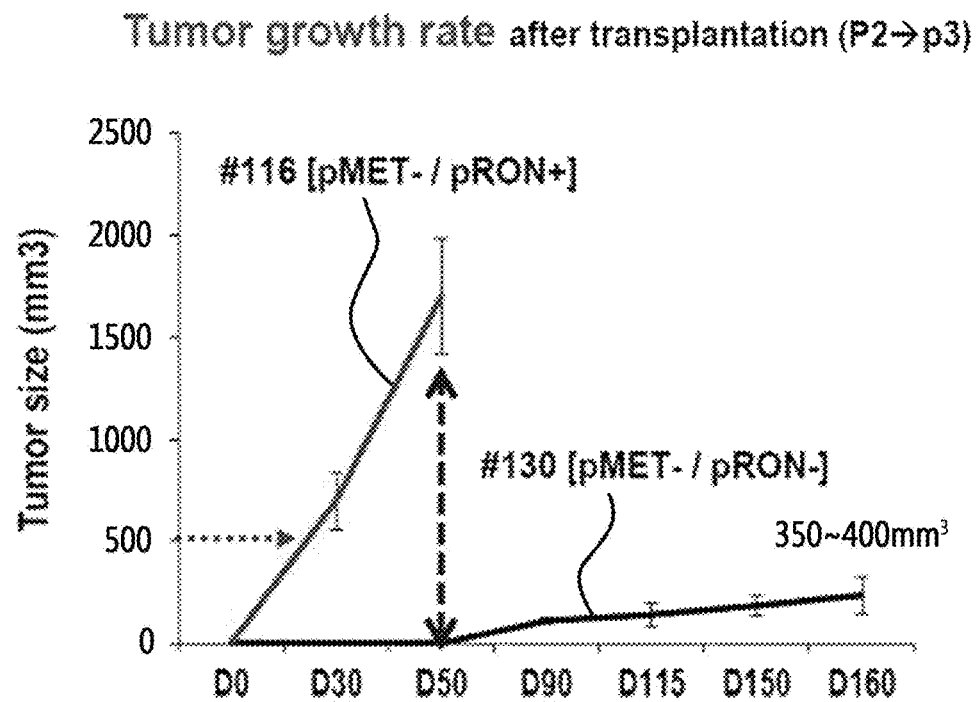

[Fig. 3a]
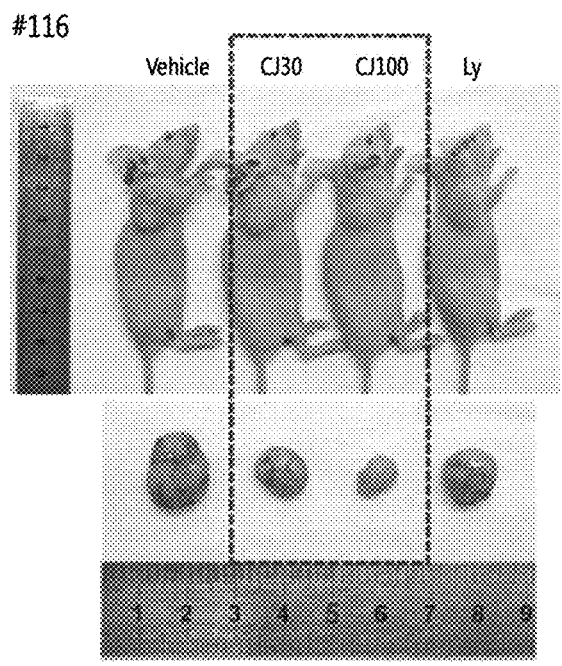
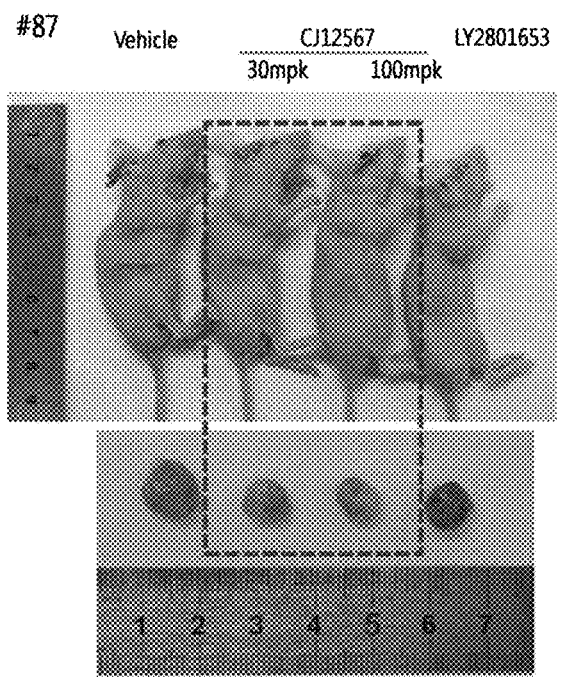

[Fig. 3b]
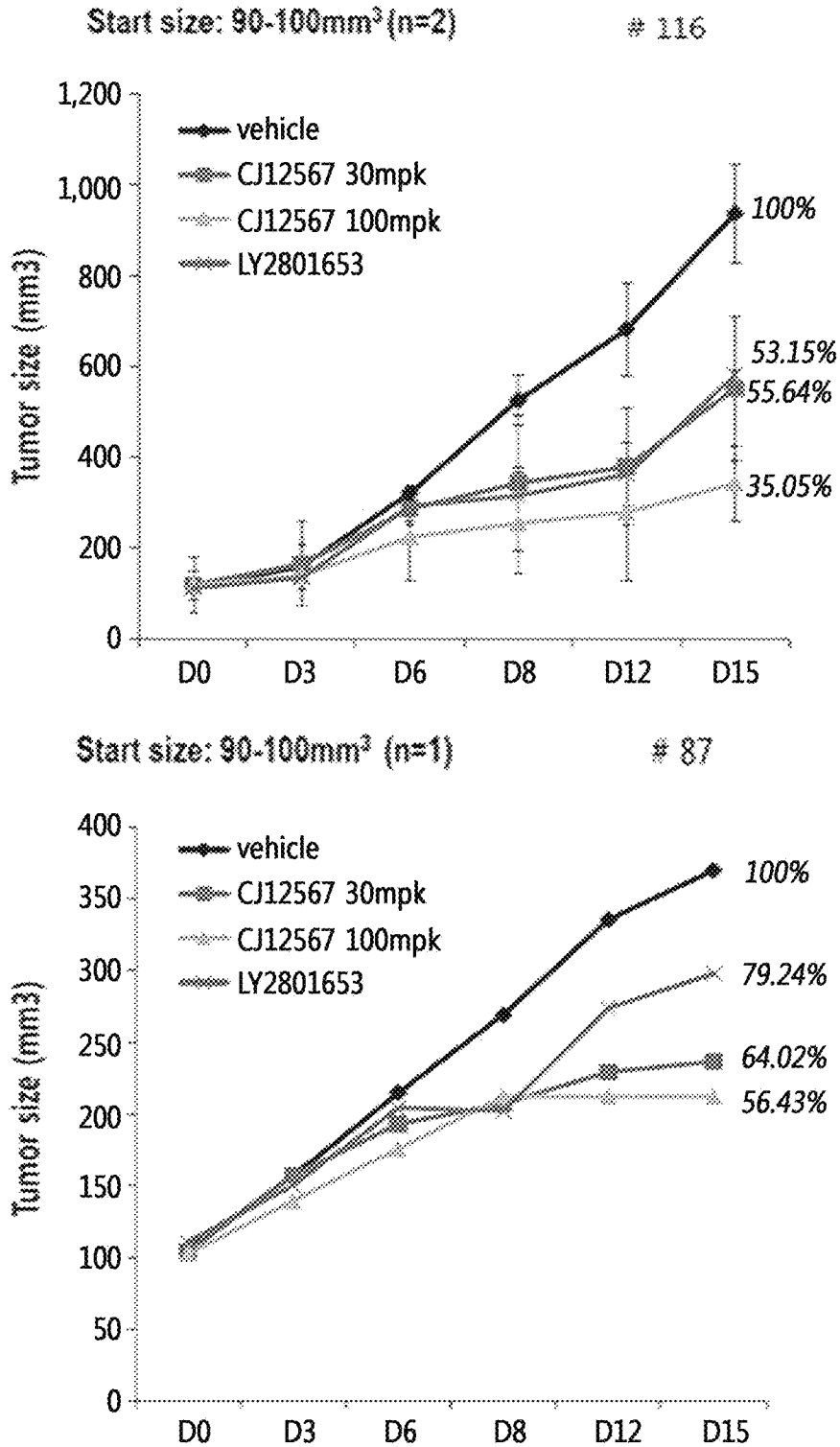

| Group | | tumor weight (%) |
|---|---|---|
| vehicle | | 100 |
| CJ12567 | 30mpk | 47.87 |
| | 100mpk | 18.09 |
| LY2801653 | | 63.83 |

87

| Group | | tumor weight (%) |
|---|---|---|
| vehicle | | 100 |
| CJ12567 | 30mpk | 61.36 |
| | 100mpk | 40.91 |
| LY2801653 | | 70.45 |

[Fig. 3d]
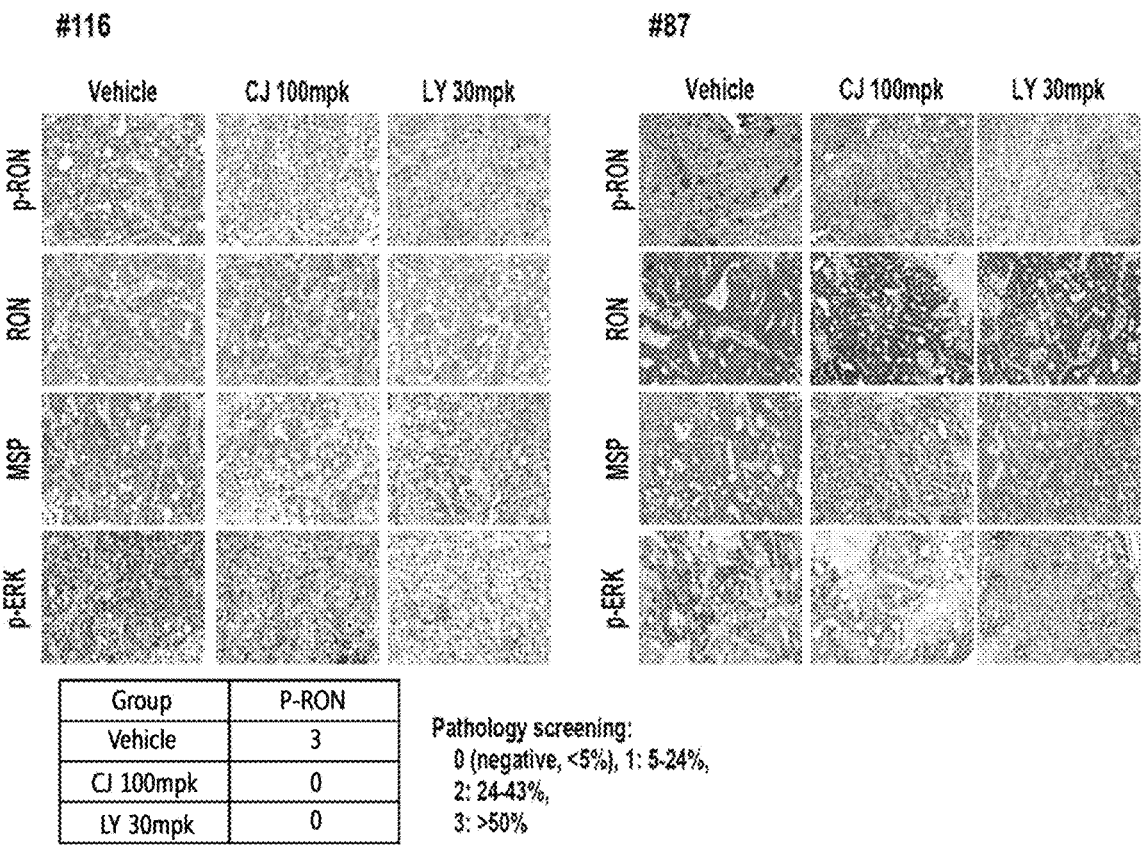

[Fig. 3e]
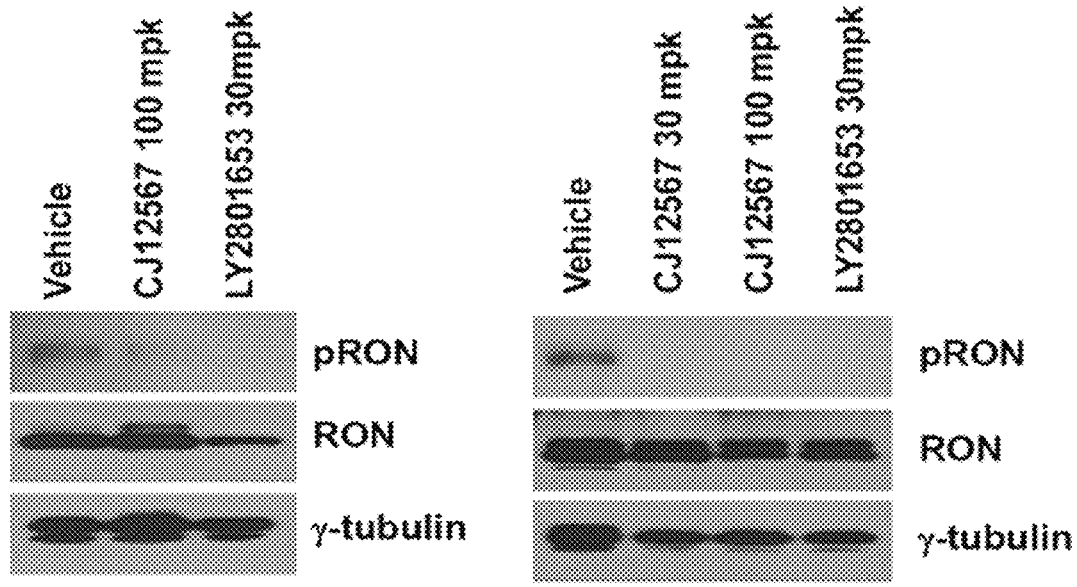

[Fig. 4a]
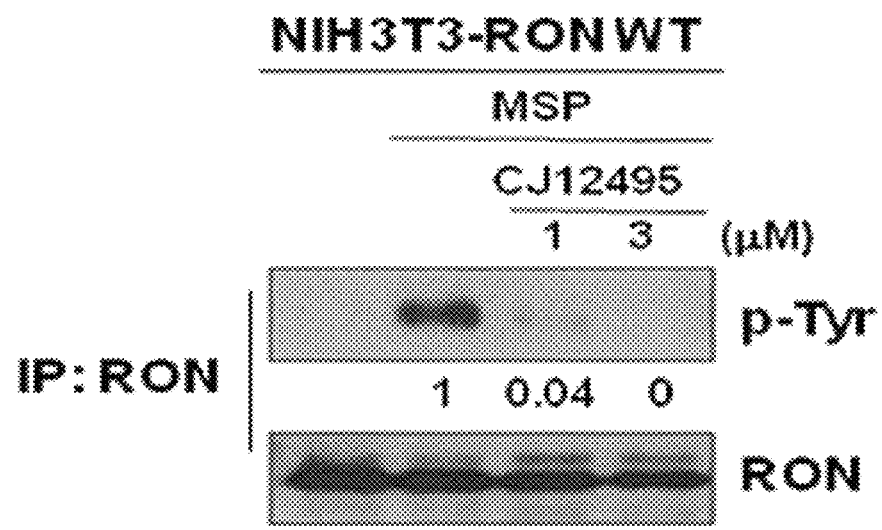

[Fig. 4b]
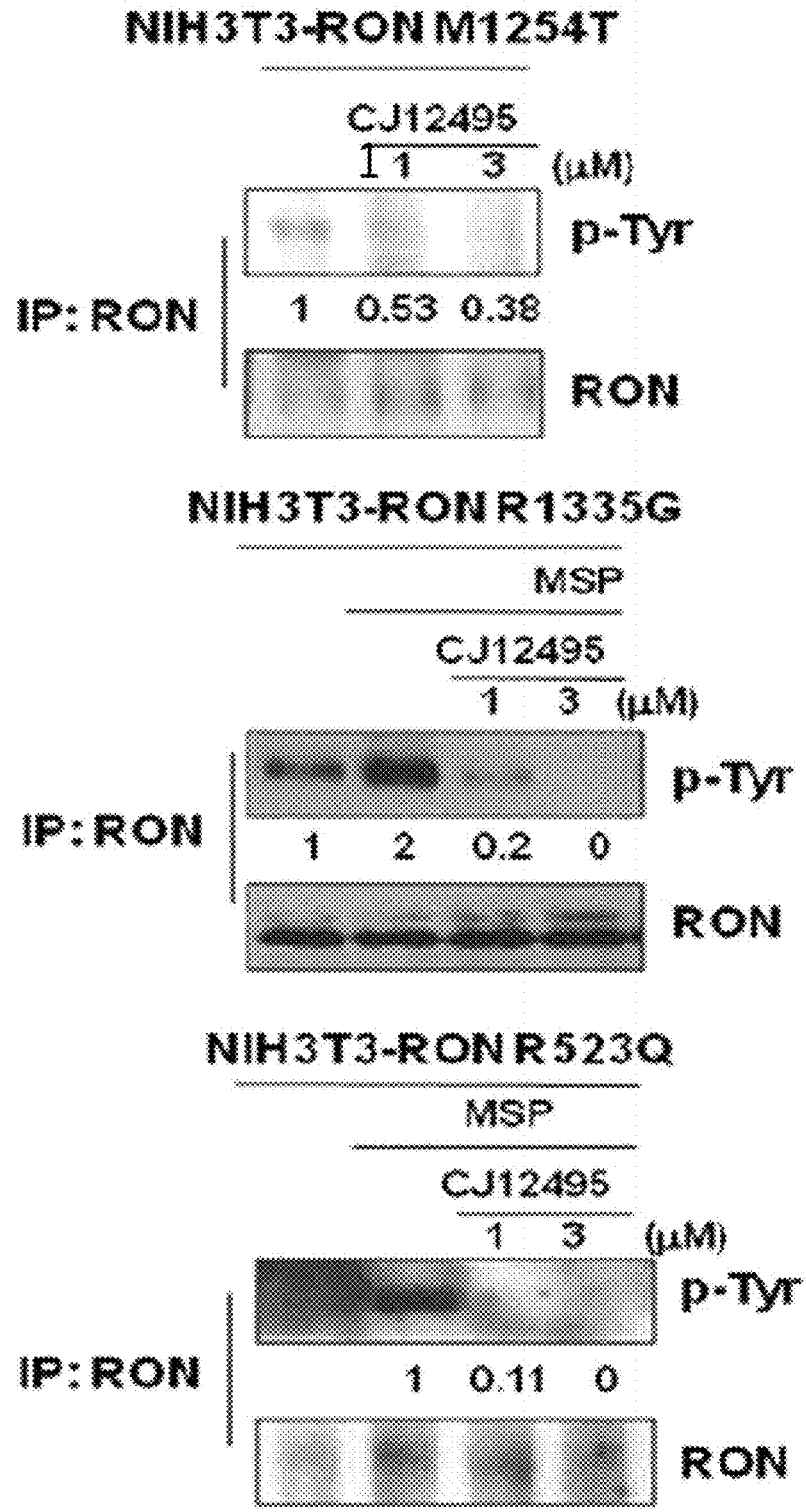

[Fig. 4c]
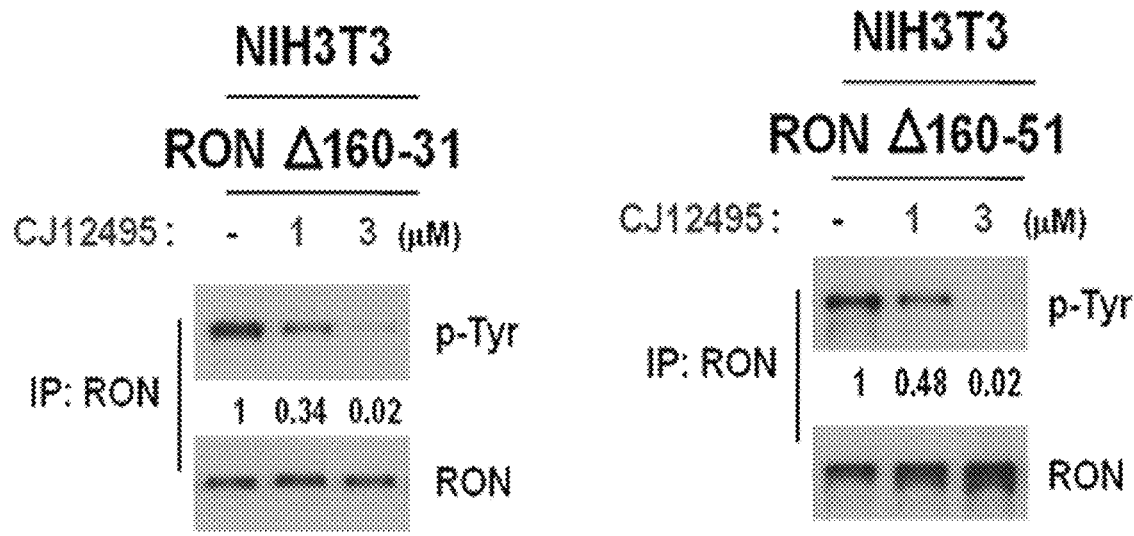
[Fig. 4d]
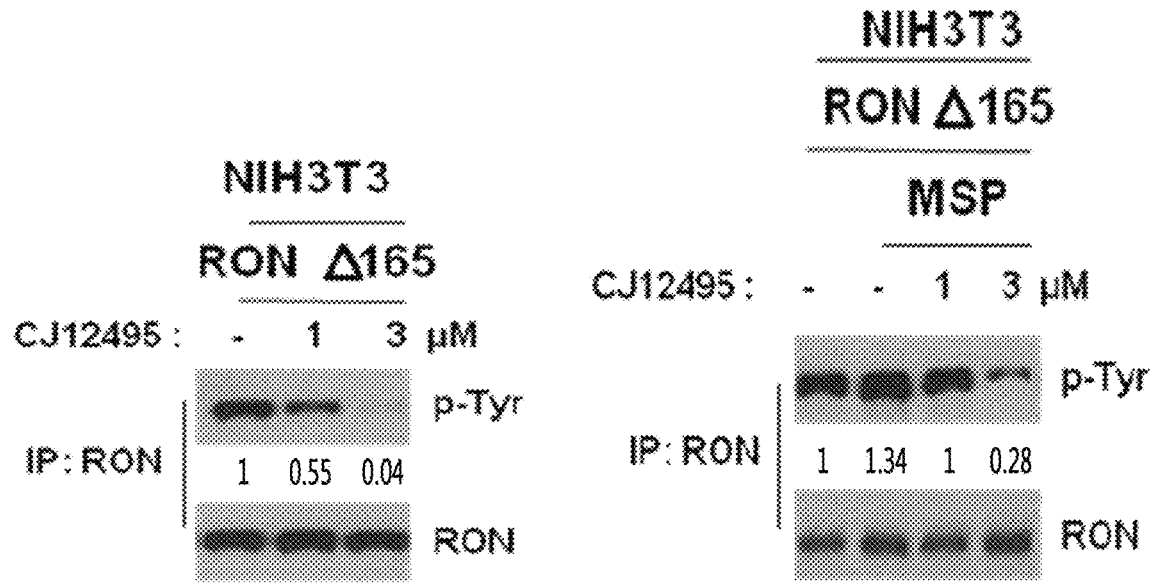

[Fig. 5a]
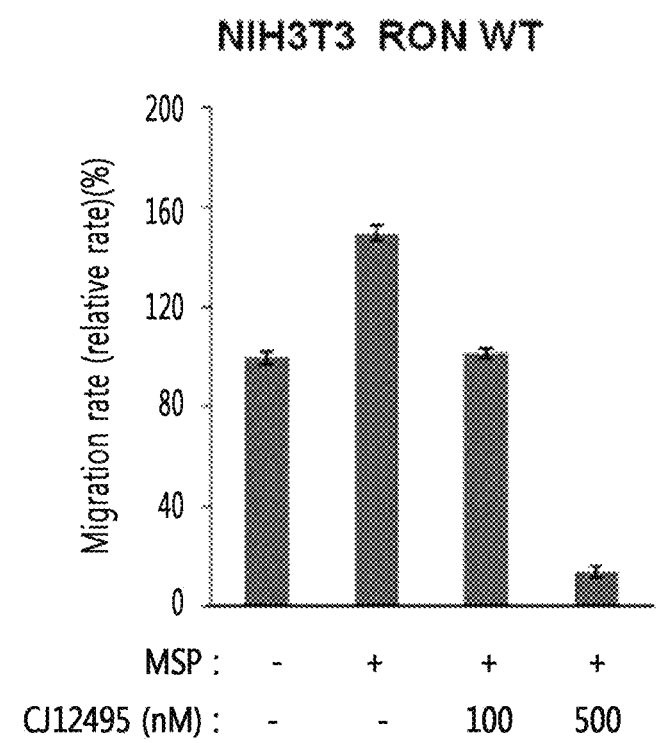

[Fig. 5b]
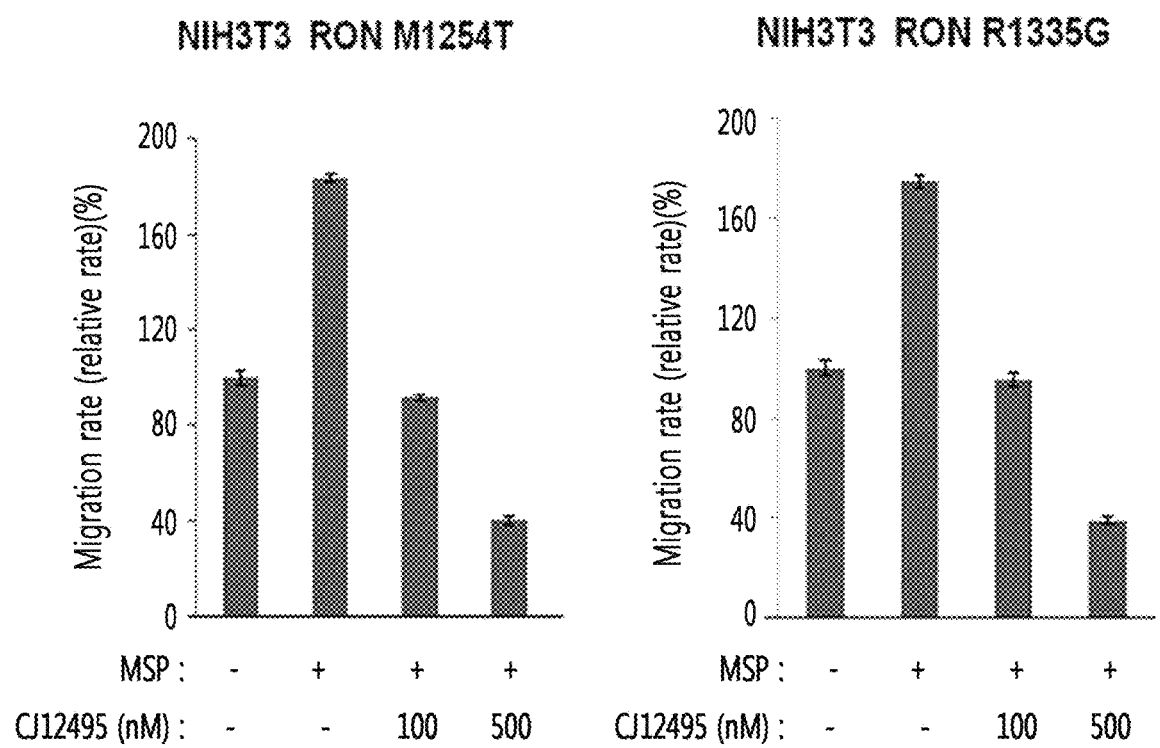

[Fig. 5c]
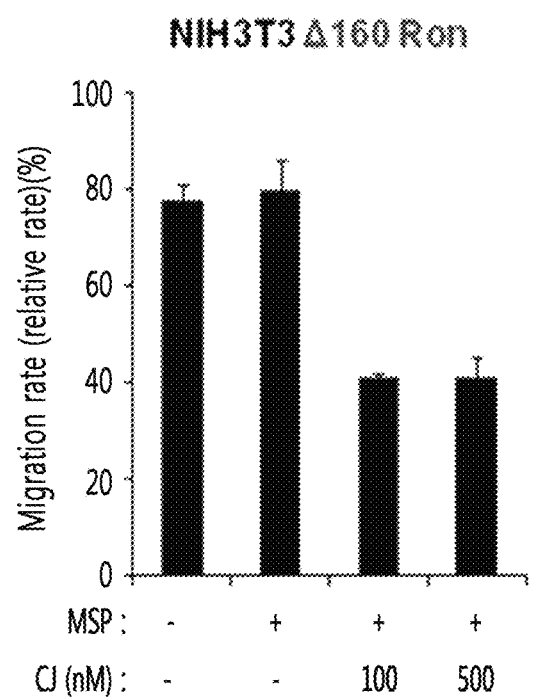
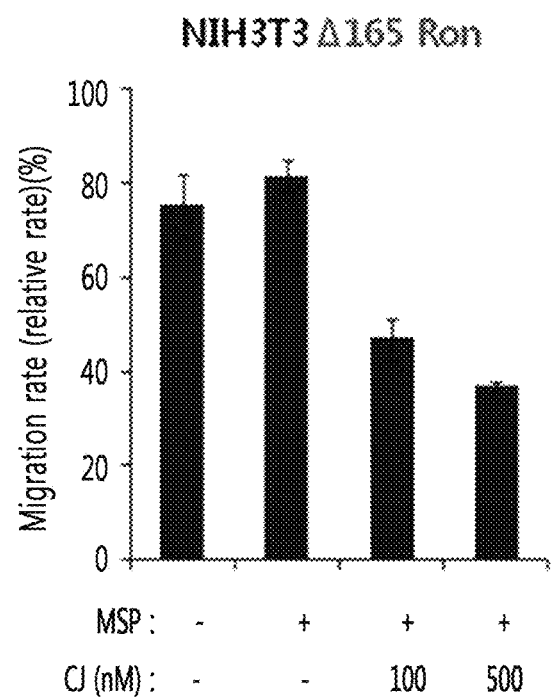

[Fig. 6a]
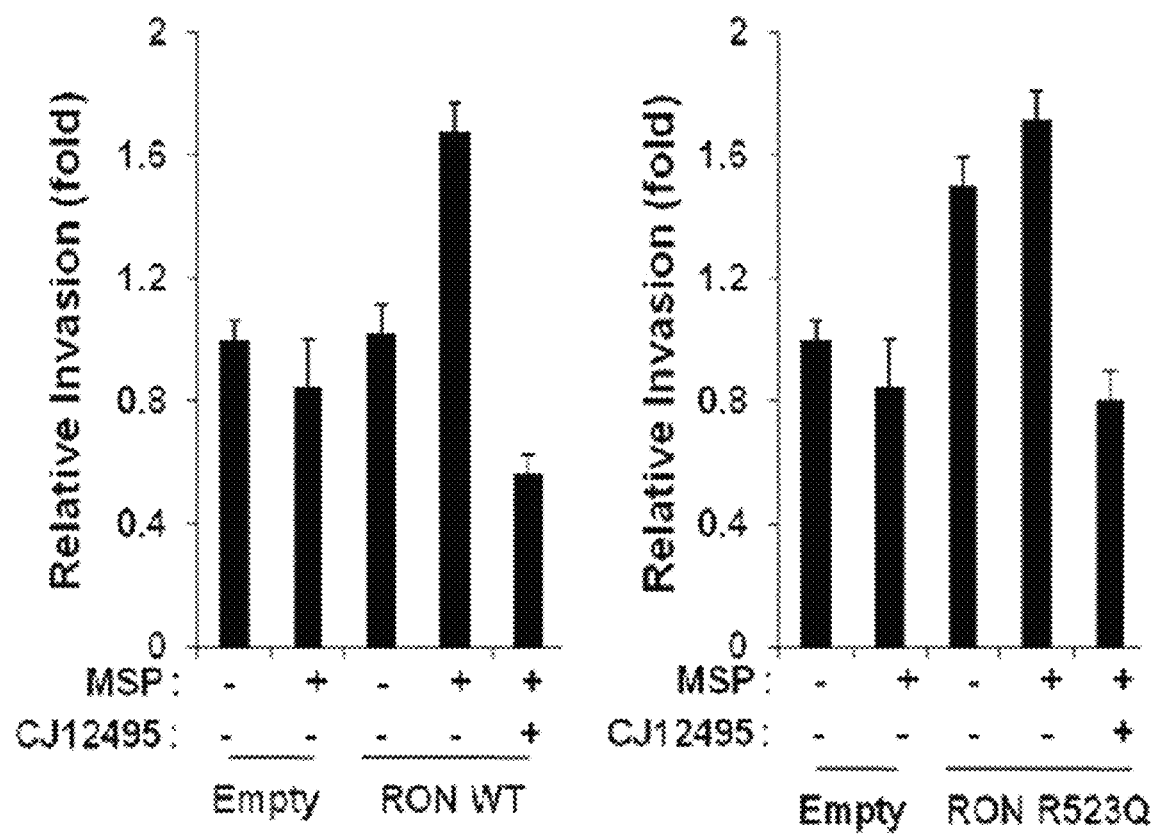

[Fig. 6b]
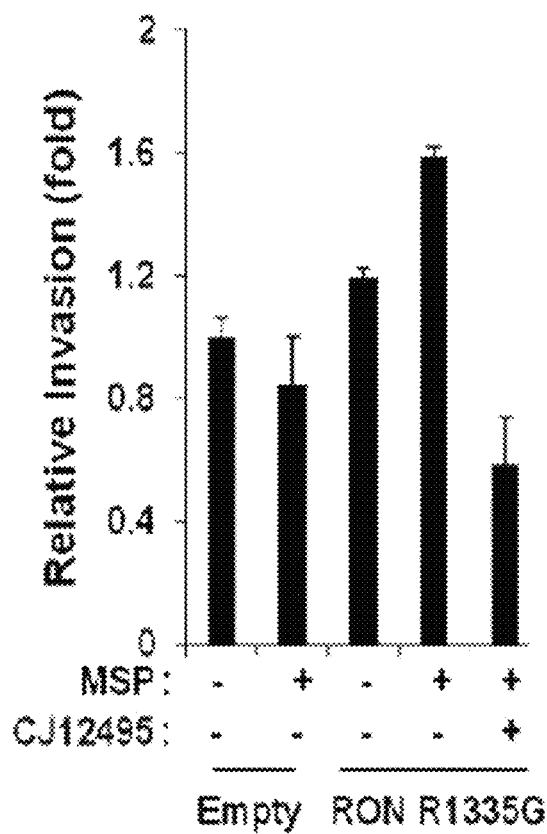
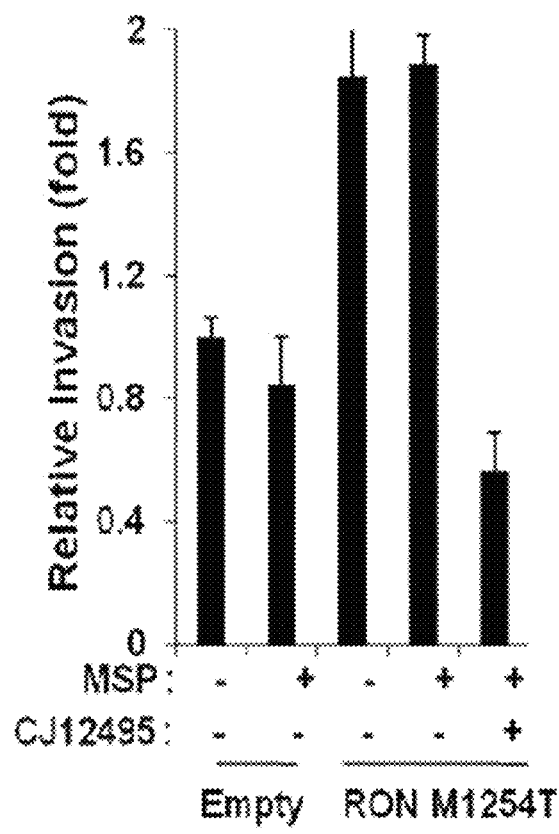

[Fig. 6c]
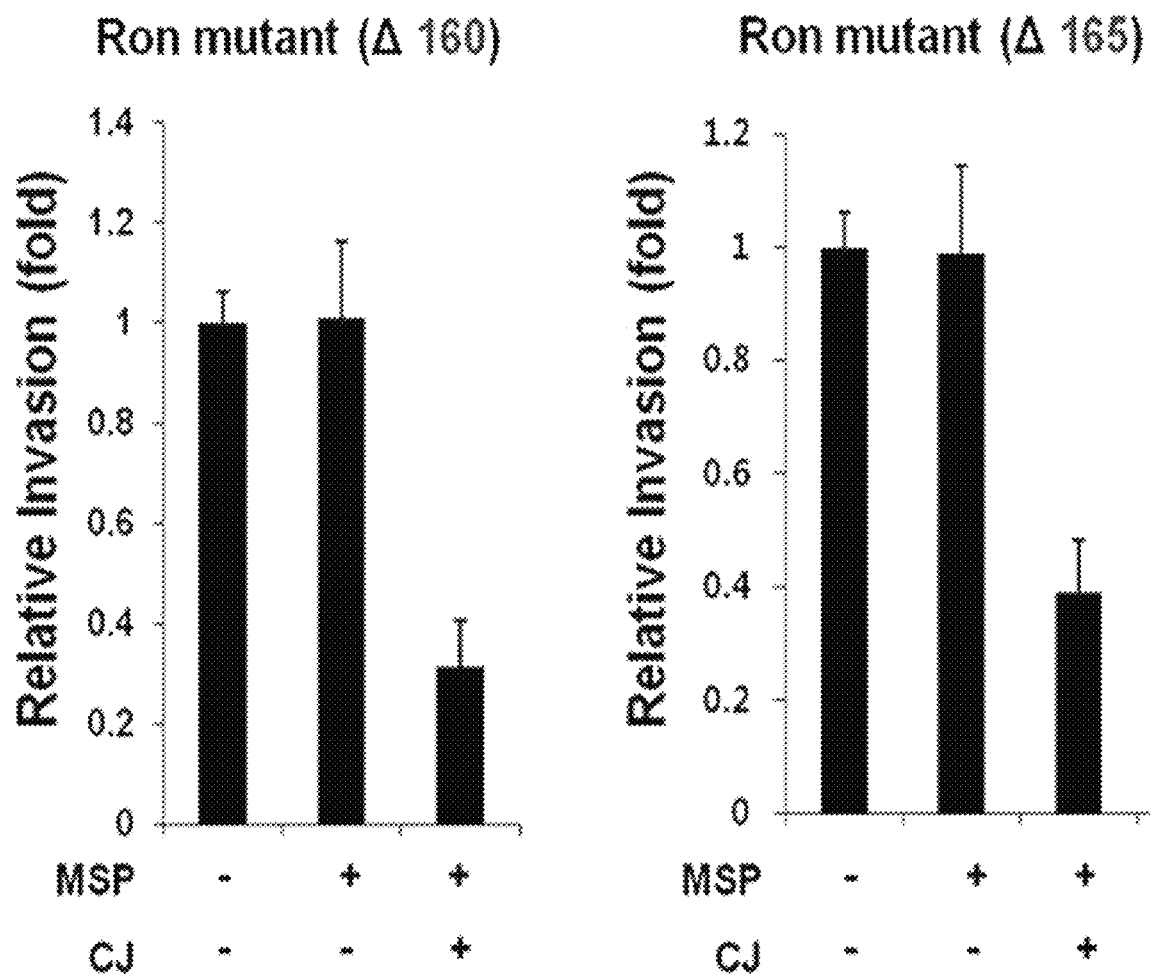

[Fig. 7a]
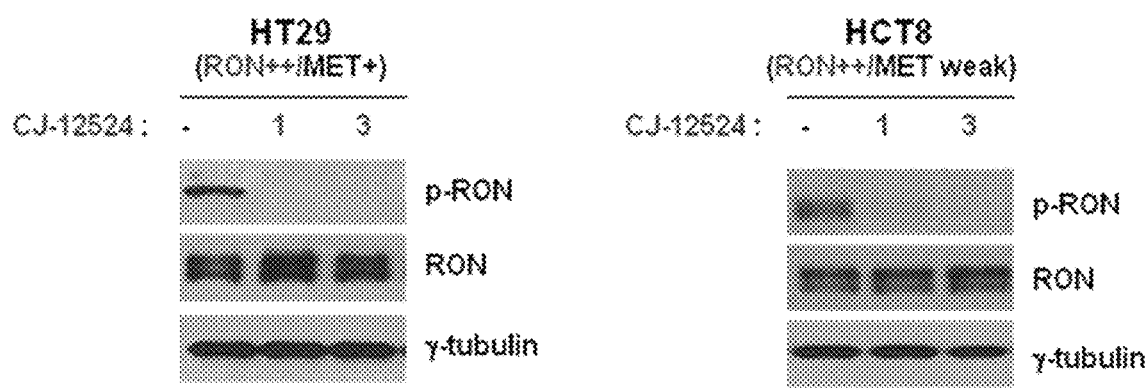
[Fig. 7b]
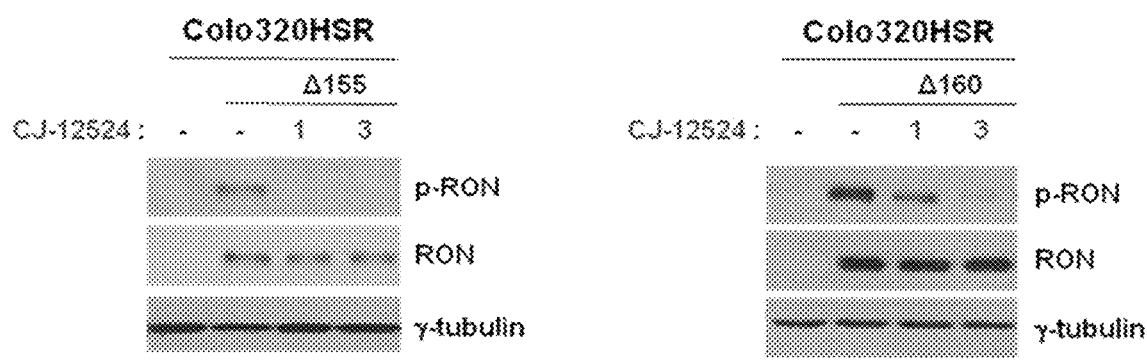

[Fig. 7c]
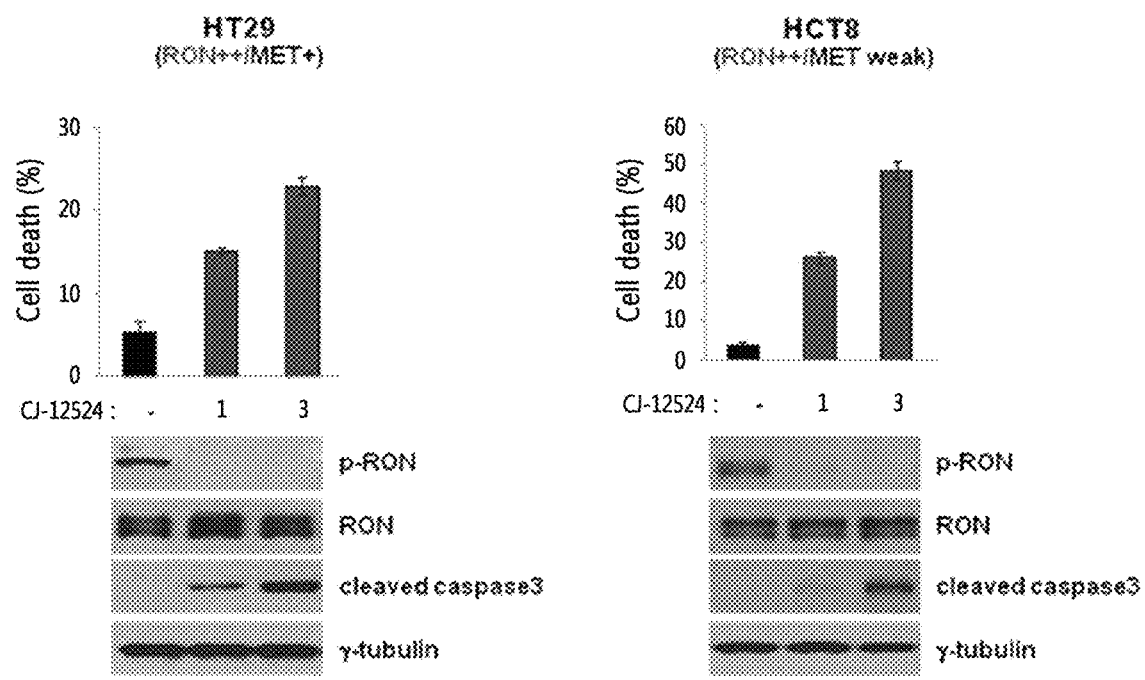

[Fig. 7d]
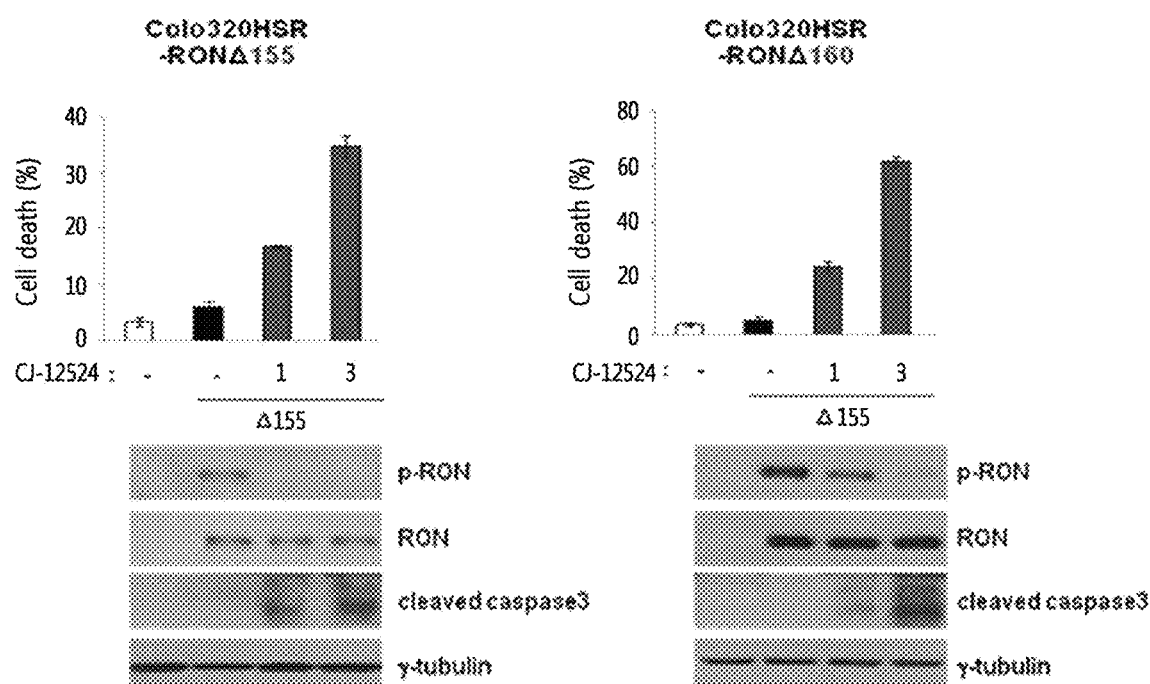

[Fig. 7e]
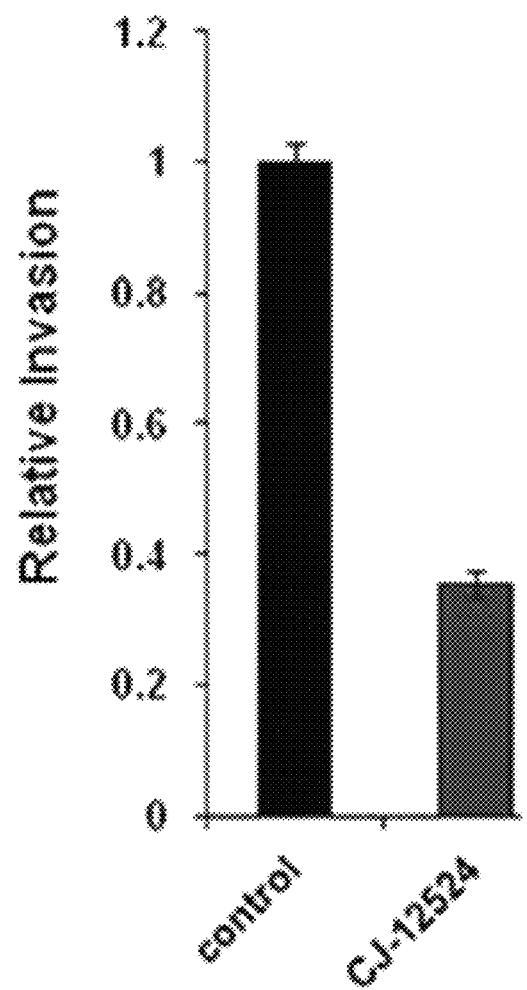

[Fig. 8a]
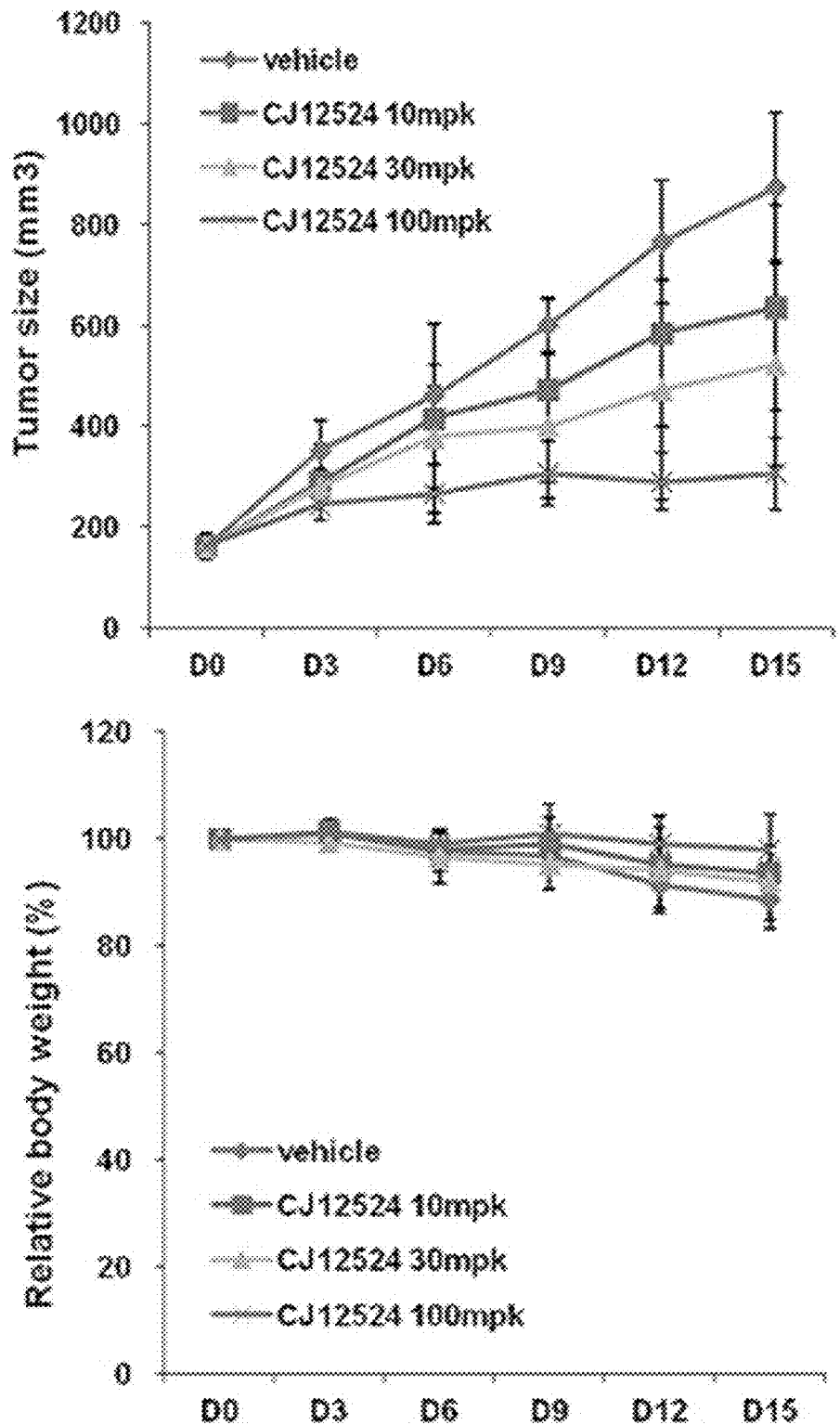

[Fig. 8b]
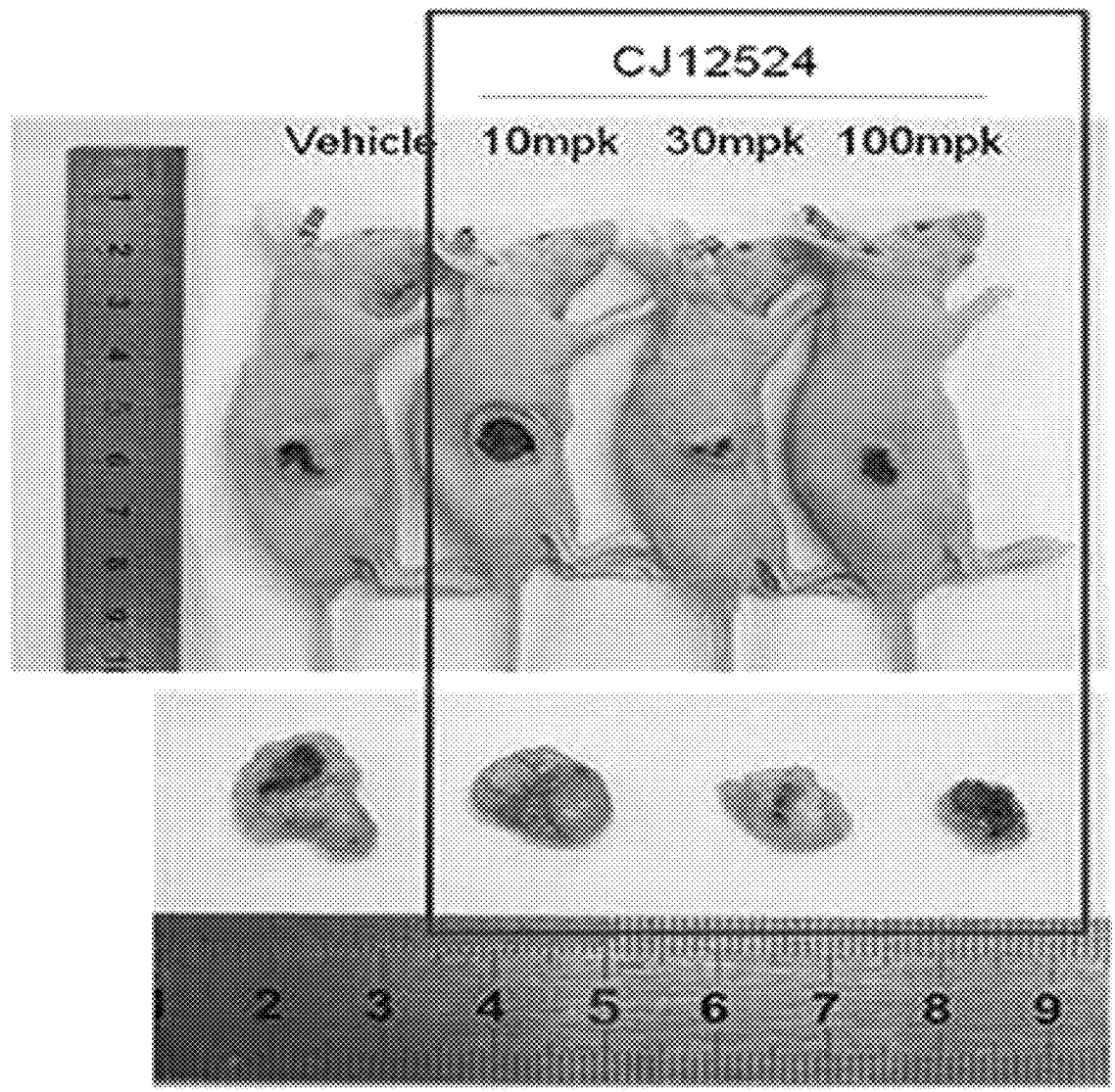
|  | tumor weight (g) | tumor weight (%) |
| --- | --- | --- |
| vehicle | 0.4 | 100 |
| CJ12524 10mpk | 0.21 | 52.5 |
| CJ12524 30mpk | 0.17 | 42.5 |
| CJ12524 100mpk | 0.09 | 22.5 |

[Fig. 8c]
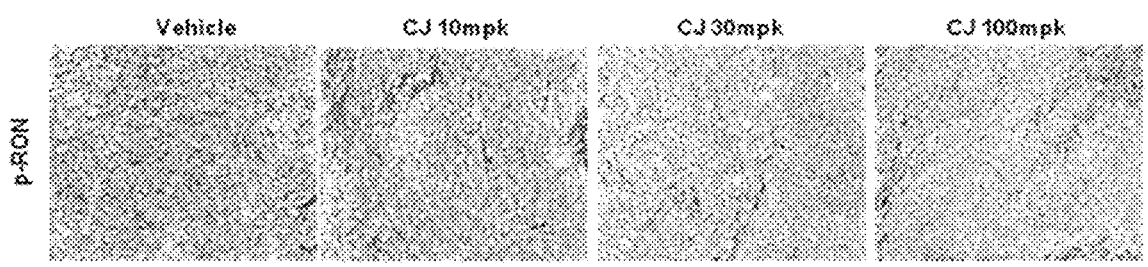
[Fig. 8d]
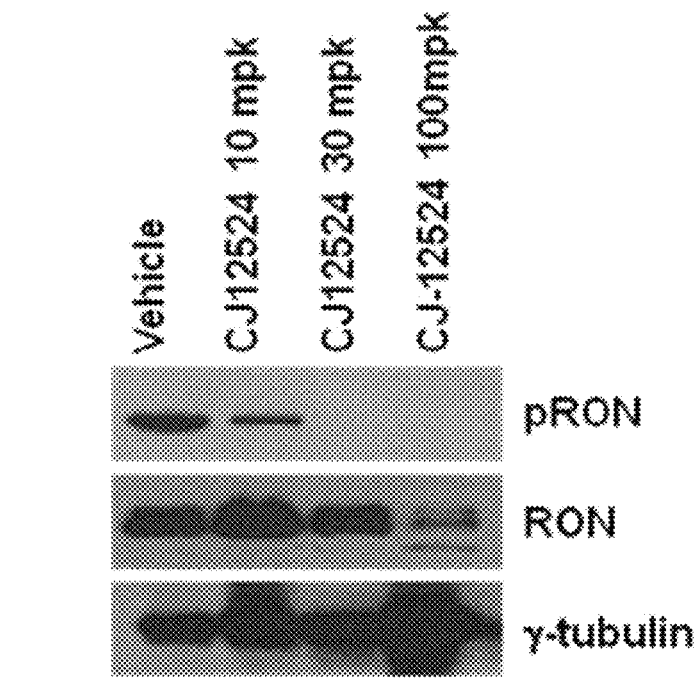

[Fig. 9]
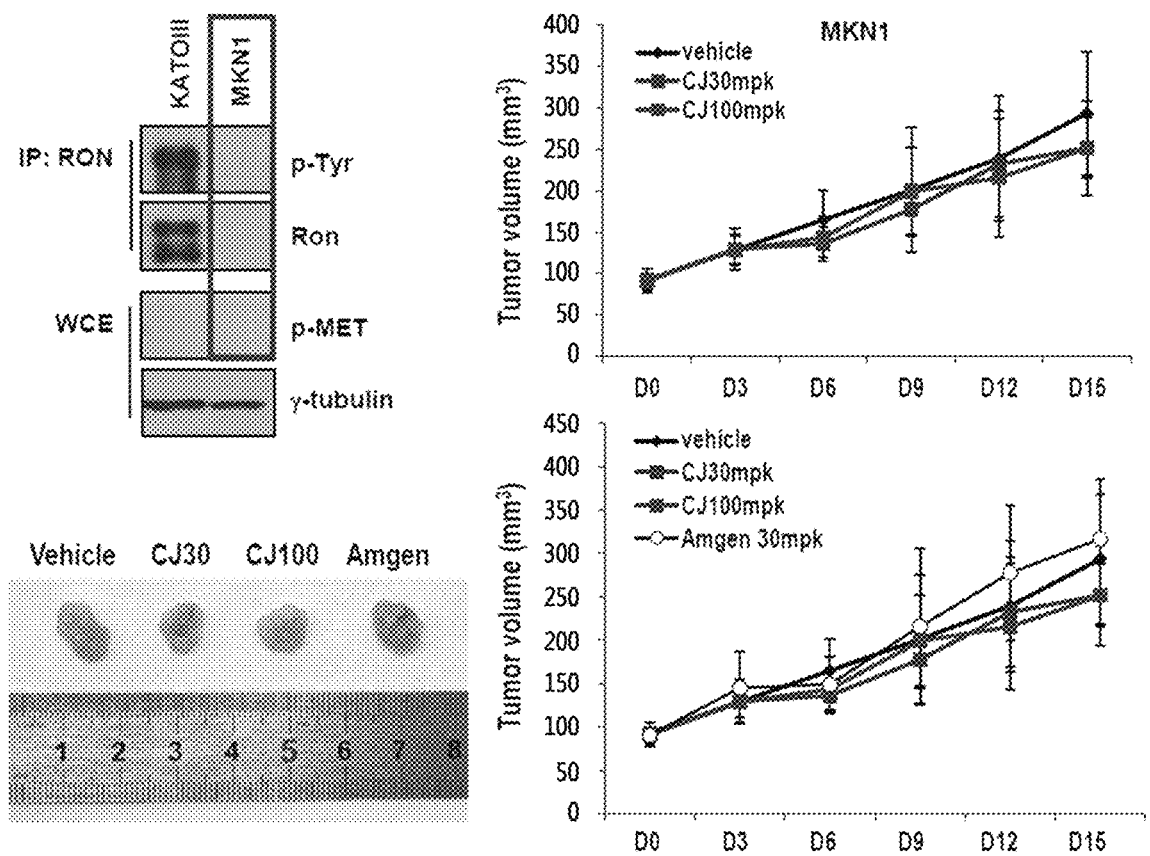

BIOMARKER FOR PREDICTING THE SENSITIVITY TO A PROTEIN KINASE INHIBITOR AND A USE THEREOF

CROSS-REFERENCES TO RELATED APPLICATIONS

This application is a U.S. national phase application of International PCT Patent Application No. PCT/KR2015/009322, which was filed on Sep. 3, 2015, which claims priority to Korean Patent Application Nos. 10-2014-0116787, filed Sep. 3, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_057_00US_ST25.txt. The text file is 27 KB, was created on Mar. 3, 2017, and is being submitted electronically via EFS-Web.

TECHNICAL FIELD

The present disclosure relates to a biomarker for predicting the sensitivity to a protein kinase inhibitor and a use thereof.

BACKGROUND ART

Generally, with respect to anticancer therapy, in-vivo reactivity to an anticancer drug largely depends on the sensitivity of cancer cells, which are being targeted by the drug, to the drug. Such sensitivity of cancer cells to a given drug varies greatly from cancer cell to cancer cell. The sensitivity of cancer cells is ascribed to the quantitative or qualitative difference in the target molecules of the drug or factors involved therein, acquirement of drug resistance, etc. Based on such background, it will be very beneficial to confirm the genetic change of cancer cells, which appears specifically when the cancer cells exhibit the sensitivity to a given anticancer drug, because the confirmation would enable early determination of the effect of a drug, establishment of therapies, selection of a new therapy, etc. Additionally, it would be very useful from the clinical view to measure the presence of the sensitivity of a given cancer cell to a drug based on the genetic change by treating the cancer cell with the drug after separating the cancer cell from cancer tissue obtained before treatment from biopsy tissue, etc., according to a conventional method, because the measurement would enable the prediction of the effectiveness of the drug in the treatment.

Meanwhile, a protein kinase is an enzyme that regulates the activity, location, and function of other proteins by phosphorylation, thereby controlling the various intracellular processes. The abnormalities in the function of the protein kinase are closely associated with mechanisms of diseases such as cancer, immune disease, neurological disease, metabolic disease, infections, etc. Examples of the protein kinase may include Abl, ACK, ALK, Arg, ARK5, Aurora, Axl, Bmx, BTK, CDK, CHK, c-Kit, c-MET, c-RAF, c-SRC, EGFR, FAK, Fes, FGFR, Flt3, GSK3, IGF, IKK, JAK, Lck, LIMK, Lyn, MEK, Mer, MK-2, P38alpha, PDGFR, PDK, Pim, PKA, PKB, PKCR, Plk-⅓, Ret, RON, Ros, Rse, Tie, Trk, Tyro3, VEGFR, YES, etc.

Among these, with regard to c-MET, the aberrant activation of c-MET is closely associated with the deterioration of the prognosis of anticancer treatment, and the overexpression and mutation of c-MET are observed in various kinds of cancer such as non-small cell lung cancer. Since the invasion and metastasis of a tumor is a major cause of death in cancer patients, inhibition of c-MET signaling is expected to be effective for cancer treatment.

Recepteur d'Origine Nantais (RON) is a protein receptor belonging to the MET (c-MET) series. It is secreted in the liver and is a receptor for a serum protein (macrophage-stimulating protein, MSP), which regulates the actions of macrophage (Zhou Y Q, He C, Chen Y Q, Wang D, Wang M H: Altered expression of the RON receptor tyrosine kinase in primary human colorectal adenocarcinomas: generation of different splicing RON variants and their oncogenic potential. Oncogene 2003, 22 (2):186-197). RON expression is abnormally regulated in breast cancer and colorectal cancer, and specifically, it is closely associated with metastasis of colorectal cancer. The degree of RON activity is regulated by alternative splicing, which is one of the major processes in regulating the gene expression of eukaryotic organisms. RONΔ155, RONΔ160, and RONΔ165 are the forms generated by skipping of exons by such splicing and they are always in a structurally-active state even without a ligand.

Additionally, the mutation of RON gene is correlated with the occurrence and grade of various kinds of cancer.

CJ12495, CJ12537, CJ12524, and CJ12567, which are described in Korean Patent No. 10-1350006, are anticancer drugs capable of inhibiting abnormal proliferation of cancer cells, and they are inhibitors capable of inhibiting the activities of the protein kinases.

As described above, anticancer drugs show individual differences with respect to resistance and toxicity and have a problem in that more than about half of patients show resistance, and thus the selection of a suitable treatment-reactive marker can bring about an innovative improvement. Accordingly, studies on the reactivity to treatment of individual cancer drugs according to particular genes are being actively and continuously developed at present.

However, the achievement is still negligible due to the complex actions of factors associated with in-vivo reactions to particular drugs, diversity of treatment drugs and administration modes, and difficulties in obtaining sufficient samples.

DISCLOSURE

Technical Problem

Under the circumstances, the present inventors have made efforts to develop a biomarker capable of predicting the sensitivity to a protein kinase inhibitor, which is an anticancer drug against colon cancer. As a result, they have analyzed variants and mutants of RON gene and the sensitivity according to activation of RON gene and confirmed that the degree of decrease in size and weight of cancer cell by the sensitivity to a particular drug varied in colon cancer cells according to the RON activation or expression features of the variants and mutants of RON gene, thereby completing the present disclosure.

Accordingly, in an object, the present disclosure provides a biomarker for predicting the sensitivity to protein kinase inhibitors, a composition, a kit, and a method thereof.

Technical Solution

To achieve the above object, an object of the present disclosure provides a biomarker for predicting the sensitivity to protein kinase inhibitors, including active Recepteur d'Origine Nantais (RON).

Additionally, the present disclosure provides a composition for predicting the sensitivity to protein kinase inhibitors, containing an agent for measuring the expression level of active RON.

Additionally, the present disclosure provides a kit for predicting the sensitivity to a protein kinase inhibitor including the composition.

Additionally, the present disclosure provides a method for predicting the sensitivity to a protein kinase inhibitor.

Advantageous Effects of the Invention

The use of the biomarker of the present disclosure for predicting the sensitivity to protein kinase inhibitors can determine with certainty the sensitivity of an individual patient before the initiation of treatment, and thus it is possible to select an anticancer drug with a high therapeutic effect. Additionally, the use of anticancer drugs without a noticeable effect can be avoided, and thus unnecessary side-effects can be prevented.

DESCRIPTION OF DRAWINGS

FIG. 1a shows the RT-PCR results for wild-type RON or RONΔ155 or RONΔ160 variants in colon cancer cell lines (HT29, colo320hsr, and MKN28) and a colon cancer patient's sample. FIG. 1b shows the results of western blot and immunoprecipitation (IP) for wild-type RON or RONΔ155 or RONΔ160 variants in colon cancer cell lines (HT29, colo320hsr, and MKN28) and a colon cancer patient's sample. FIG. 1c shows the IHC results for P-RON in a colon cancer patient's sample.

FIG. 2a shows a schematic diagram illustrating the process of a drug sensitivity test in a PDX-model. FIG. 2b shows the measurement results of the tumor size in a case when the $116^{th}$ sample, which is a sample of a colon cancer patient determined to be positive with regard to the RON variants during the process of the PDX-model preparation, was transplanted, and the tumor size in a case when the $130^{th}$ sample, which was not determined to be positive with regard to the RON variants during the process of the PDX-model preparation, was transplanted.

FIG. 3a shows the images of cancer tissue formed in a nude mouse when CJ12567 was administered into a patient-derived colon cancer tissue xenograft model (PDX-model), which is a nude mouse transplanted with the $87^{th}$ and $116^{th}$ samples of colon cancer patients. FIG. 3b shows the measurement results of the size of tumor tissues obtained from the above mice. FIG. 3c shows the measurement results of the weight of tumor tissues obtained from the above mice. FIG. 3d shows the IHC results of the tumor tissues obtained from the above mice. FIG. 3e shows the western blotting results of the tumor tissues obtained from the above mice.

FIG. 4a shows the inhibition of RON phosphorylation by CJ12495. FIG. 4b shows the inhibition of RON phosphorylation in a cell introduced with a RON mutant gene. FIG. 4c shows the inhibition of RON phosphorylation in a RON gene variant. FIG. 4d shows the inhibition of RON phosphorylation in a RON gene variant.

FIG. 5a shows the inhibition of cell motility by CJ12495. FIG. 5b shows the inhibition of cell motility in a cell introduced with a RON mutant gene. FIG. 5c shows the inhibition of cell motility in a RON gene variant.

FIG. 6a shows the inhibition of cell metastasis by CJ12495. FIG. 6b shows the inhibition of cell metastasis in a cell introduced with a RON mutant gene. FIG. 6c shows the inhibition of cell metastasis in a RON gene variant.

FIG. 7a shows the inhibition of RON phosphorylation by CJ12524. FIG. 7b shows the inhibition of RON phosphorylation in a RON gene variant. FIG. 7c shows the apoptosis by CJ12524. FIG. 7d shows the apoptosis in a RON gene variant. FIG. 7e shows the inhibition of cell metastasis by CJ12524.

FIG. 8a shows the measurement results of size and weight of the tumor tissues obtained from the mice after the administration of CJ12524 to a RON-active cancer cell-xenograft model. FIG. 8b shows the images of the size of tumor tissues formed in the mice. FIG. 8c shows the IHC results of the tumor tissues obtained from the mice. FIG. 8d shows the western blotting results of the tumor tissues obtained from the mice.

FIG. 9 shows the measurement results of tumor volume after the administration of CJ12537 to a RON-inactive stomach cancer cell-xenograft model.

BEST MODE

Hereinafter, the present disclosure is explained in greater detail.

In an aspect, the present disclosure provides a biomarker for predicting the sensitivity to protein kinase inhibitors, including active Recepteur d'Origine Nantais (RON).

As used herein, the term "Recepteur d'Origine Nantais (RON)" refers to a protein receptor belonging to the MET (c-MET) series, which is secreted in the liver and acts as a receptor for a serum protein (macrophage-stimulating protein, MSP), which regulates the actions of macrophage. RON protein and RON gene are known in the art and can be obtained from a known database. Specifically, the sequences of RON protein may be those disclosed in GenBank No. NP_002438.2 and the sequences of RON genes may be those disclosed in GenBank No. NM_002447.1.

In the present disclosure, it was confirmed that the sensitivity to a protein kinase inhibitor becomes higher when RON is in an activated state or present in an active form. Accordingly, active RON can be used as a biomarker. The active RON may be understood as a concept to encompass all that can be confirmed as the active form in all expression levels such as levels of DNA, mRNA, protein, etc. In an exemplary embodiment, the active RON may be RON with phosphorylation, for example, the active RON may be present in a form where the RON protein is phosphorylated in the kinase domain, thus being present in an active form, or the active RON may be in a form which was induced to an active form in the presence of a ligand such as MSP. Additionally, the active RON may include a splicing variant or mutant of RON gene, in which the RON is always in an activated form.

Accordingly, in an exemplary embodiment, the present disclosure provides a biomarker for predicting the sensitivity to protein kinase inhibitors, including a splicing variant or mutant of RON gene.

As used herein, the term "variant" refers to a RON isoform which was formed by the deletion of the exon region(s) of the corresponding gene by alternative splicing.

In a preferred embodiment of the present disclosure, the variant of the present disclosure may be one in which at least one selected from the group consisting of exons 5, 6, and 11 of the RON gene is deleted by alternative splicing. More preferably, the variant of the present disclosure may be RONΔ155 (a variant where the exons 5, 6, and 11 of the RON gene are deleted), RONΔ160 (a variant where the exons 5 and 6 of the RON gene are deleted), or RONΔ165 (a variant where the exon 11 of the RON gene is deleted).

The variant RONΔ155 of the RON gene is represented by SEQ ID NO: 1, RONΔ160 by SEQ ID NO: 2, and RONΔ165 by SEQ ID NO: 3.

According to the present disclosure, the splicing variants, where exons are deleted by alternative splicing mechanism of the RON gene, are frequently discovered specifically in cells and tissues of human colon cancer patients, and their sensitivity to drugs varies according to their expression.

As used herein, the term "mutant" includes those in which the nucleotides or an amino acid sequence of the corresponding gene underwent base substitution, deletion, insertion, amplification, and rearrangement. The nucleotide modification indicates a change in the nucleotide sequence with respect to the reference sequence (e.g., a wild-type sequence), for example, insertion, deletion, inversion, or substitution of at least one nucleotide, such as single-nucleotide polymorphism (SNP). This term, unless otherwise indicated, may also include changes in the complement of the nucleotide sequence. The nucleotide modification may be a somatic mutation or germline polymorphism.

Additionally, the amino acid modification may indicate a change in the amino acid sequence with respect to the reference sequence (e.g., a wild-type sequence), for example, insertion, substitution, or deletion of at least one amino acid, such as internal deletion or N- or C-terminus truncation.

In a preferred embodiment, the mutant of the present disclosure may be one in which the amino acid in the polypeptide of SEQ ID NO: 4 is substituted, deleted, or inserted.

In a preferred embodiment, the mutant of the present disclosure may be at least one selected from the group consisting of a mutant in which the 1254$^{th}$ amino acid in the polypeptide of SEQ ID NO: 4 is substituted from M to T; a mutant in which the 1335$^{th}$ amino acid in the polypeptide of SEQ ID NO: 4 is substituted from R to G; a mutant in which the 523$^{rd}$ amino acid in the polypeptide of SEQ ID NO: 4 is substituted from R to Q; a mutant in which the 1232$^{nd}$ amino acid in the polypeptide of SEQ ID NO: 4 is substituted from D to V; and a mutant in which the 1268$^{th}$ amino acid in the polypeptide of SEQ ID NO: 4 is substituted from M to T.

The biomarker of the present disclosure can be an indicator for the sensitivity to protein kinase inhibitors, which are anticancer drugs. Since the biomarker of the present disclosure has excellent accuracy and fidelity to anticancer drugs for a sensitive marker, it can be used for the treatment of occurrence, development, and/or metastasis of cancer.

As used herein, the term "sensitivity" means whether a particular drug exhibits any effect against the cancer of individual cancer patients.

For example, the particular drug mostly refers to anticancer drugs, and among these anticancer drugs, some drugs are known to exhibit anticancer effects while others do not. Additionally, even for the cancer against which the drugs are shown to be effective, it is known that the drugs may or may not be effective depending on individual patients. The presence of the effect of anticancer drugs for individual cancer patients is called anticancer drug sensitivity. Accordingly, if it is possible to predict the patients according to the present disclosure before the initiation of treatment, whether the drug effect is expected to be shown in the patients (responsive patients) or the effect of the drug is not expected to be shown in the patients (non-responsive patients), a chemotherapy with high effectiveness and safety can be practiced.

As used herein, the term "prediction" is used to indicate the possibility of whether a drug or drug set may react advantageously or disadvantageously for a subject patient. In an aspect, the prediction may relate to the degree of such reactivity. For example, the prediction relates to the survival of a patient without cancer recurrence after treatment with a particular therapeutic agent and/or a surgical removal of primary tumor and/or chemotherapy for a predetermined period of time, and/or the probability thereof. The prediction of the present disclosure may be used clinically in determining the treatment by selecting the most appropriate treatment method for colon cancer patients. The prediction of the present disclosure is a useful tool for predicting whether the patient can advantageously react to therapeutic treatment, for example, a given therapeutic treatment (e.g., administration of a given therapeutic agent or combined agent, an introduction of surgery, chemotherapy, etc.) or whether the patient can survive long-term after therapeutic treatment.

In a preferred embodiment of the present disclosure, the protein kinase may be at least one selected from the group consisting of Abl, ACK, ALK, Arg, ARK5, Aurora, Axl, Bmx, BTK, CDK, CHK, c-Kit, c-MET, c-RAF, c-SRC, EGFR, FAK, Fes, FGFR, Flt3, GSK3, IGF, IKK, JAK, Lck, LIMK, Lyn, MEK, Mer, MK-2, P38alpha, PDGFR, PDK, Pim, PKA, PKB, PKCR, Plk-⅓, Ret, RON, Ros, Rse, Tie, Trk, Tyro3, VEGFR, and YES, more specifically, c-MET, c-RAF, c-SRC, EGFR, FAK, Fes, FGFR, MEK, Mer, MK-2, P38alpha, PDGFR, PDK, Pim, PKA, PKB, PKCR, Plk-⅓, Ret, or RON, and most specifically, c-MET and RON.

In a preferred embodiment of the present disclosure, the protein kinase inhibitor may be at least one selected from the group consisting of CJ12495, CJ12537, CJ12524, CJ12567, K252a, SU11274, PHA-665752, ARQ-197, PF-02341066, PF-04217903, JNJ-38877605, Foretinib, SGX523, MP470, AMG102, AMG706, LY2801653, XL-184, Flavopihdol, Olomoucine, Roscovitine, Purvanolols, CGP74514A, Roscovitine, Bevacizumab, Cetuximab, Gefitinib, Erlotinib, Panitumumab, PM-166, EKB-569, HM-272 (WAY-177820), Lapatinib, Canertinib, AEE788, XL647, BMS 5599626, and Zactima, more specifically, CJ12495, CJ12537, CJ12524, CJ12567, K252a, SU11274, PHA-665752, ARQ-197, PF-02341066, PF-04217903, JNJ-38877605, Foretinib, SGX523, MP470, AMG102, AMG706, LY2801653, or XL-184, and most specifically, CJ12495, CJ12537, CJ12524, or CJ12567.

The above-described CJ12495, CJ12537, CJ12524, and CJ12567 are inhibitors suppressing the activities of protein kinases as described in Korean Patent No. 10-1350006, which is incorporated herein as a reference. In the present disclosure, CJ12495, CJ12537, CJ12524, and CJ12567 are used as anticancer drugs having the function of inhibiting the abnormal proliferation of cancer cells.

Specifically, the protein kinase inhibitors of the present disclosure may be a compound represented by the following Formula 1, which is described in Korean Patent No. 10-1350006, or a salt thereof.

[Formula 1]

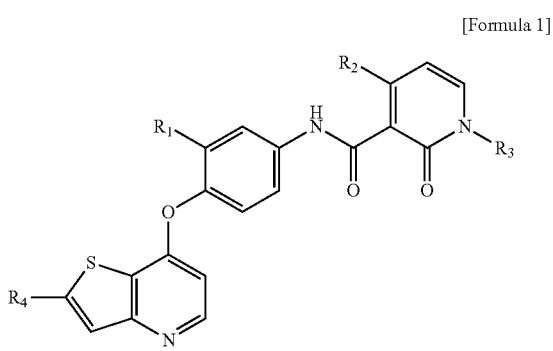

More specifically, CJ12495, being a protein kinase inhibitor of the present disclosure, is "4-ethoxy-N-(3-fluoro-4-(2-(1-methyl-1H-imidazol-4-yl)thieno[3,2-b]pyridin-7-yloxy)phenyl)-1-(4-fluorophenyl)-2-oxo-1,2-dihydropyridin-3-carboxamide" prepared in Example 1 of Korean Patent No. 10-1350006, and may be a compound represented by Formula 2 shown below. Additionally, CJ12537 is a HCl salt of CJ12495, i.e., a HCl salt of "4-ethoxy-N-(3-fluoro-4-(2-(1-methyl-1H-imidazol-4-yl)thieno[3,2-b]pyridin-7-yloxy)phenyl)-1-(4-fluorophenyl)-2-oxo-1,2-dihydropyridin-3-carboxamide".

[Formula 2]

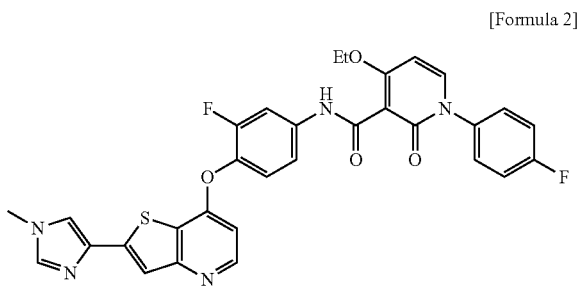 [SMILES: CCOc1ccn(-c2ccc(F)cc2)c(=O)c1C(=O)Nc1ccc(Oc2ccnc3cc(-c4cn(C)cn4)sc23)c(F)c1]

Additionally, more specifically, CJ12524, being a protein kinase inhibitor of the present disclosure, is "4-ethoxy-N-(3-fluoro-4-(2-(pyridin-2-yl)thieno[3,2-b]pyridin-7-yloxy)phenyl)-1-(4-fluorophenyl)-2-oxo-1,2-dihydropyridin-3-carboxamide" prepared in Example 8 of Korean Patent No. 10-1350006, and may be a compound represented by Formula 3 shown below. Additionally, CJ12567 is a HCl salt of CJ12524, i.e., a HCl salt of "4-ethoxy-N-(3-fluoro-4-(2-(pyridin-2-yl)thieno[3,2-b]pyridin-7-yloxy)phenyl)-1-(4-fluorophenyl)-2-oxo-1,2-dihydropyridin-3-carboxamide".

[Formula 3]

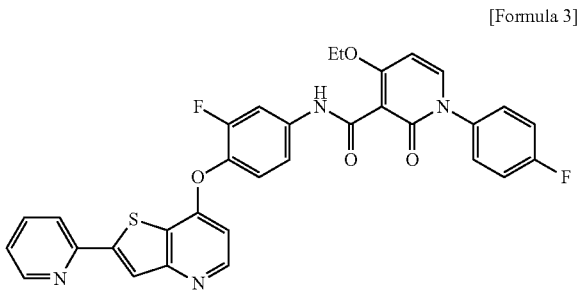 [SMILES: CCOc1ccn(-c2ccc(F)cc2)c(=O)c1C(=O)Nc1ccc(Oc2ccnc3cc(-c4ccccn4)sc23)c(F)c1]

According to another aspect, the present disclosure provides a composition for predicting the sensitivity to a protein kinase inhibitor containing an agent for measuring the expression level of active Recepteur d'Origine Nantais (RON). The active RON is the same as explained above, and specifically, the expression level of active RON may include that of a splicing variant or mutant. In the present disclosure, the expression level of active RON may be understood to refer to all kinds of expression levels including those in levels of DNA, mRNA, protein, etc.

According to a preferred embodiment, the protein kinase inhibitors of the present disclosure may be a therapeutic agent for cancer, psoriasis, rheumatoid arthritis, inflammatory bowel disease, or chronic obstructive pulmonary disease.

According to a preferred embodiment, the cancer may be at least one selected from the group consisting of ACTH-producing cancer, acute lymphocytic or lymphoblastic leukemia, acute or chronic lymphocytic leukemia, acute non-lymphocytic leukemia, bladder cancer, brain tumor, breast cancer, cervical canal cancer, chronic myeloid leukemia, intestinal cancer, T-zone lymphoma, endometriosis, esophageal cancer, biliary bladder cancer, Ewing's sarcoma, head and neck cancer, tongue cancer, Hodgkin's lymphoma, Kaposi's sarcoma, kidney cancer, liver cancer, lung cancer, mesothelioma, multiple myeloma, neuroblastoma, non-Hodgkin's lymphoma, osteosarcoma, ovarian cancer, mammary cancer, prostate cancer, pancreatic cancer, colon cancer, penine cancer, retinoblastoma, skin cancer, stomach cancer, thyroid cancer, uterine cancer, testis cancer, Wilms' tumor, and trophoblastoma. More specifically, the cancer may be at least one selected from the group consisting of neuroblastoma, non-Hodgkin's lymphoma, osteosarcoma, ovarian cancer, mammary cancer, cervical canal cancer, prostate cancer, pancreatic cancer, colon cancer, penine cancer, retinoblastoma, skin cancer, stomach cancer, thyroid cancer, uterine cancer, testis cancer, Wilms' tumor, and trophoblastoma, and most specifically, colon cancer.

As used herein, the term "colon cancer" collectively refers to rectal cancer, colorectal cancer, and anal cancer.

In the present disclosure, unless stated otherwise, the expression "measurement of an expression level" refers to detecting a subject to be detected in a given sample. In the present disclosure, the subject to be detected may include the activated form of the corresponding protein within the given sample, and may include both the mRNA and/or protein of a variant of mutant of a gene. That is, the presence of expression can be confirmed by detecting RNA, which is a product of a gene variant or mutant, or a protein, which is a gene product as well as by detecting the activated form of the protein.

The detection may be performed by a conventional extraction of RNA or a protein from a sample or by detecting RNA or a protein present in the extract. The detection of RNA or a protein may be measured by an immunoassay method, a hybridization method, and an amplification method, but the detection method is not limited thereto and the detection can be easily performed using various technologies known in the art.

According to a preferred embodiment of the present disclosure, the agent for measuring the expression level may include an antisense oligonucleotide, a primer pair, or a probe which specifically binds to mRNA, and in particular, to mRNA of the splicing variant or mutant.

The agent for measuring the presence of the mRNA expression may be selected from the group consisting of an antisense oligonucleotide, a primer pair, and a probe, which are specific to the above gene, and a combination thereof. That is, the detection of a nucleic acid may be performed by at least one amplification reaction, which employs at least one oligonucleotide primer that is hybridized with a nucleic acid molecule encoding a gene or a complementary product of the nucleic acid molecule.

For example, the detection of mRNA using a primer may be performed by confirming the presence of amplification of a gene by a method known in the art, after amplifying the sequence of the gene by an amplification method such as PCR.

According to a preferred embodiment of the present disclosure, the primer pair may consist of (a) a forward primer of SEQ ID NO: 5; and (b) a reverse primer of SEQ ID NO: 6.

Additionally, according to a preferred embodiment of the present disclosure, the agent for measuring the expression level may include a RON protein, for example, an antibody, a peptide, or a nucleotide, which specifically binds to active RON or a mutant protein. Additionally, the agent for measuring the expression level may include an antibody for detecting RON phosphorylation to confirm the presence of an active form of the RON protein.

The agent for measuring the presence of expression of the protein refers to an antibody that specifically binds to the proteins, and may include all of a polyclonal antibody, a monoclonal antibody, a recombinant antibody, and a combination thereof.

The antibody may not only include a polyclonal antibody, a monoclonal antibody, a recombinant antibody, and a complete form of an antibody having two full-length light chains and two full-length heavy chains, but may also include all of the functional fragments of an antibody molecule, e.g., Fab, F(ab'), F(ab')2, and Fv. The antibody may be easily prepared using a technology known in the art to which the present disclosure belongs, and any antibody prepared and available on the commercial market may also be used.

Although the composition of the present disclosure contains an agent for measuring the presence of expression of the above-described gene, the composition may further contain a label enabling quantitative or qualitative measurement of formation of an antigen-antibody complex, a conventional device used for immunoassays, a reagent, etc.

Examples of the label enabling quantitative or qualitative measurement of the antigen-antibody complex formation may include enzymes, fluorescent materials, ligands, light-emitting materials, microparticles, redox molecules, radioactive isotopes, etc., but is not limited thereto. Examples of the enzymes to be used as a detection label may include β-glucuronidase, β-D-glucosidase, β-D-galactosidase, urease, peroxidase, alkaline phosphatase, acetylcholinesterase, glucose oxidase, hexokinase and GDPase, RNase, glucose oxidase and luciferase, phosphofructokinase, phosphoenolpyruvate carboxykinase, aspartate aminotransferase, phosphoenolpyruvate decarboxykinase, β-lamatase, etc., but are not limited thereto. Examples of the fluorescent materials may include fluorescein, isothiocyanate, rhodamine, phycoerythrin, phycocyanin, allophycocyanin, o-phthalaldehyde, fluorescamine, etc., but are not limited thereto. Examples of the ligands may include biotin derivatives, but are not limited thereto. Examples of the light-emitting materials may include acridinium ester, luciferin, luciferase, etc., but are not limited thereto. Examples of the microparticles may include colloidal gold, colored latex, etc., but are not limited thereto. Examples of the redox molecules may include ferrocenes, ruthenium complexes, viologens, quinones, Ti ions, Cs ions, diimides, 1,4-benzoquinone, hydroquinone, K4 W(CN)$_8$, [Os(bpy)$_3$]$^{2+}$, [RU(bpy)$_3$]$^{2+}$, [MO(CN)$_8$]$^{4-}$, etc., but are not limited thereto. Examples of the radioactive isotopes may include $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, $^{186}$Re, etc., but are not limited thereto.

Examples of the device or reagent may include an appropriate carrier, solubilizer, cleaner, buffer, stabilizer, but are not limited thereto. When the labeling material is an enzyme, a substrate enabling the measurement of enzyme activity and a reaction terminator may be included. The carrier may be a soluble carrier or insoluble carrier. Examples of the soluble carrier may include a physiologically acceptable buffer known in the art, e.g., PBS. Examples of the insoluble carrier may include polystyrene, polyethylene, polypropylene, polyester, polyacrylonitrile, fluoro resin, crosslinked dextran, polysaccharide, paper, glass, metal, agarose, and a combination thereof.

Since the composition of the present disclosure contains the biomarker described above as an active ingredient, the repeated description of the content is omitted herein to avoid excessive complexity of the present disclosure.

According to another aspect, the present disclosure provides a kit for predicting the sensitivity to a protein kinase inhibitor including the composition.

The kit may include not only the agent for measuring the expression level of a gene but also a tool, a reagent, etc., generally used in the art for immunoassays.

In an exemplary embodiment of the tool or reagent may include a labeling material capable of forming a detectable signal, a chromophore, a solubilizer, a cleaner, a buffer, a stabilizer, etc., but is not limited thereto. When the labeling material is an enzyme, a substrate enabling the measurement of enzyme activity and a reaction terminator may be included. The carrier may be a soluble carrier or insoluble carrier. Examples of the soluble carrier may include a physiologically acceptable buffer known in the art, e.g., PBS. Examples of the insoluble carrier may include polystyrene, polyethylene, polypropylene, polyester, polyacrylonitrile, fluoro resin, crosslinked dextran, polysaccharide, paper, glass, metal, agarose, and a combination thereof.

Since the composition of the present disclosure contains the biomarker described above as a constitution, the repeated description of the content is omitted herein to avoid excessive complexity of the present disclosure.

According to still another aspect, the present disclosure provides a method for predicting the sensitivity to a protein kinase inhibitor, including (a) measuring the expression level of active Recepteur d'Origine Nantais (RON) within a biological sample obtained from a subject; and (b) determining the sensitivity of the subject to a protein kinase inhibitor based on the result measured in step (a).

The expression level of the active RON to be measured is the same as explained above, and specifically, it may include the expression level of a splicing variant or mutant of RON gene.

According to a preferred embodiment of the present disclosure, in the case when the expression of the active RON of step (a) is confirmed, the subject is determined to have the sensitivity to the protein kinase inhibitor.

The prediction method of the present disclosure is performed by obtaining a biological sample obtained from a subject patient; measuring the expression level of one or a plurality selected from the group consisting of variants or mutants of the RON gene within the sample; and upon confirmation of the expression, determining that the corresponding sample has the sensitivity to a protein kinase inhibitor.

That is, the prediction method of the present disclosure is characterized in that the presence of expression of a particular variant or mutant within a sample is used as an index for the sensitivity for an anticancer drug for cancer cells.

Additionally, according to a preferred embodiment of the present disclosure, in the case when the expression level of the active RON of step (a) is higher than that of the control group, the subject is determined to have the sensitivity for the protein kinase inhibitor.

The present disclosure may further include comparing the expression level of the sample to that of the control group.

The prediction method of the present disclosure is performed by obtaining a biological sample obtained from a subject patient; measuring the expression level of one or a plurality selected from the group consisting of variants or mutants of the RON gene within the sample; and upon comparison of the expression levels and based on the expression features thereof, determining that the corresponding sample has the sensitivity to a protein kinase inhibitor.

Unless otherwise specified, as used herein, the term "control group" refers to the expression level of a variant of the corresponding gene or a protein thereof of a normal healthy person; the expression level of a wild-type of the corresponding gene or a protein thereof of a normal healthy person; the expression level of a variant of the corresponding gene or a protein thereof of a subject patient with a disease for comparison; or the expression level of a wild-type of the corresponding gene or a protein thereof of a subject patient with a disease for comparison.

More specifically, step (b) of the present disclosure is a process that the corresponding cancer cells obtained from the subject patient are determined to have the sensitivity to the protein kinase inhibitor as an anticancer agent, in the case when the expression level of active RON of the control group (e.g., a RON gene variant, mutant, or wild-type) is confirmed to be higher than that measured in step (a).

As used herein, the term "high expression" indicates the value or level of a biomarker within a biological sample, which is higher than the value or level of a biomarker detected in the biological sample obtained from a healthy or wild-type (normal) individual, in the case when the biomarker exhibits an abnormal process, a disease, or other diseased conditions in an individual, or a sign thereof. Additionally, the term "high expression" may indicate "a differential level" or "a differential value" or "expressed differently" compared to that of the "normal" expression level or value of a biomarker, and may include both the quantitative difference and qualitative difference in expression level.

According to a preferred embodiment of the present disclosure, the high expression means that the expression level of the subject is increased 1.2 fold compared to that of the control group.

In the present disclosure, the presence and expression of variants and mutants of the gene may affect the sensitivity to protein kinase inhibitors as described above.

The detection of the variants or mutants may be performed by target molecule cloning and sequence analysis using a technique widely known in the art, for example, DNA sequence analysis; primer extension assays such as allele-specific nucleotide incorporation assay and allele-specific primer extension assay (e.g., allele-specific PCR, allele-specific ligation chain reaction (LCR), and gap-LCR); allele-specific oligonucleotide hybridization assay (e.g., oligonucleotide ligation assay); cleavage protection assay for detecting mismatched nucleotides within the nucleic acid double helices using the protection from a cleavage agent; MutS protein binding assay; electrophoresis analysis for comparing mobility of nucleic acids of variants and wild-type; denaturing-gradient gel electrophoresis (DGGE, for example as in [Myers et al. (1985) *Nature* 313: 495]); RNase cleavage assay in mismatched base pairs; analysis of chemical or enzymatic cleavage of hetero double helix DNA; spectrophotometry (e.g., MALDITOF); Genetic Bit Analysis (GBA); 5' nuclease assay (e.g., TaqMan®); and assay using molecular beacons, but the technique is not limited thereto.

As used herein, the term "a biological sample" refers to any sample that can be obtained from a subject, in which the expression of a biomarker of the present disclosure can be detected.

The biological sample may be any one selected from the group consisting of saliva, biopsy, blood, skin tissue, liquid culture, feces, and urine. However, the biological sample is not particularly limited thereto and it may be prepared by any method conventionally used in the art.

According to the method of the present disclosure, the sensitivity is determined using the biomarker described above, and the repeated description of the content is omitted herein to avoid excessive complexity of the present disclosure.

DETAILED DESCRIPTION OF THE INVENTION

Hereinafter, the present disclosure will be described in more detail with reference to the following Examples. However, these Examples are for illustrative purposes only, and the invention is not intended to be limited by these Examples.

Experimental Methods and Conditions

RT-PCR

Total RNA was extracted from a colon cancer cell line or a sample of a human colon cancer patient by Trizol RNA extraction method and 1 μg of the total RNA was resynthesized into cDNA. Then, RT-PCR was performed using a RON primer pair (a forward primer 5'-CTCTGGGGACCAGGTTTTCC-3' of SEQ ID NO: 5 and a reverse primer 5"-ACCATCAATGGCAGGGAGTG-3' of SEQ ID NO: 6), and the PCR product was electrophoresed in 1% agarose gel and stained with ethidium bromide. The PCR conditions are shown in Table 1 below.

TABLE 1

| Temperature | Time | Number of Cycles |
| --- | --- | --- |
| 94° C. | 5 min | |
| 94° C. | 30 sec | 37 |
| 64° C. | 30 sec | |
| 72° C. | 1 min 30 sec | |
| 72° C. | 5 min | |

Western Blot

The cells in the sample were lysed using RIPA buffer and the protein was extracted therefrom using a high speed centrifuge. The protein in an amount of 30 μg per cell was separated by electrophoresis, transferred onto a PDVF membrane by western blot, and allowed to react with RON antibodies, which were diluted in 5% skim milk at a 1:2000 ratio, at 4° C. for 12 hours. Then, the resultant was washed 3 times with TBS-T buffer for 15 minutes per wash, reacted with the secondary antibodies, which were diluted in 5% skim milk at a 1:2000 ratio, at room temperature for 2 hours, washed 3 times with TBS-T buffer for 15 minutes per wash. The illumination of the PDVF membrane was induced using ECL buffer and the expression of the RON protein was developed using an X-ray film. Additionally, 1 μg of the RON antibody was added to the protein in an amount of 500 μg per cell by immunoprecipitation method, reacted at 4° C. for 12 hours, and anti-antibody beads were added thereto to immunoprecipitate the RON antibody. The resultant was separated by electrophoresis, transferred onto a PDVF membrane by western blot, and allowed to react with p-Tyr antibodies, which were diluted in 5% skim milk at a 1:1000 ratio, at 4° C. for 12 hours. Then, the resultant was washed 3 times with TBS-T buffer for 15 minutes per wash, reacted with the secondary antibodies, which were diluted in 5% skim milk at a 1:2000 ratio, at room temperature for 2 hours, and washed 3 times with TBS-T buffer for 15 minutes per wash. The illumination of the PDVF membrane was induced using ECL buffer and the expression of the p-Tyr RON protein was developed using an X-ray film.

Immunohistochemistry

Upon completion of drug administration, tissue was ablated, fixed in a 10% formalin solution, and a paraffin block was prepared therefrom on the next day. The tissue was sectioned into a size of 5 μm, treated with xylene, treated with 100%, 95%, and 70% EtOH, blocked with 3% BSA, and allowed to react with phospho-RON and RON antibody, which were each diluted in 1% BSA at a 1:100 ratio, at 4° C. for 12 hours. Then, the resultant was washed 3 times with PBS-T buffer for 15 minutes per wash, reacted with the secondary antibodies, which were diluted 1% BSA at a 1:100 ratio, at room temperature for 2 hours, washed 3 times with TBS-T buffer for 15 minutes per wash, treated with a DAB substrate, treated with hematoxylin, and subjected to a dehydration process. Then, a mount solution was dropped thereonto, it was covered with a coverslip, and the protein expression was stained.

Colon Cancer Xenograft Model (PDX-Model)

The tumor of a mouse model, which was derived from a cryopreserved patient tissue, was thawed on ice and stabilized in media, in which HBBS, 5% FBS, 1× penicillin/streptomycin, and 1× Gentamicin/amphotericin B were added. The resultant, in a size of about 3 mm$^3$, was cut out and transplanted into a skin surface of a mouse after cutting out its skin, and the surface was stitched up. After confirming tumor formation, when the tumor grew to a size of 400 mm$^3$ to 500 mm$^3$, the tissue was ablated and again cut into a size of 3 mm$^3$ and transplanted into Balb/c nude mice. After confirming tumor formation, the mice were subjected to drug administration.

Treatment With an Anticancer Drug

The anticancer drug used in the present disclosure is a c-MET inhibitor, which is CJ12567 described in Korean Patent No. 10-1350006, and LY2801653 (Lily Co.) was used as the positive control.

After confirming tumor formation, when the tumor size reached 100 mm$^3$, the experimental animals were divided into various drug administration groups and administered with CJ12567 and LY-2801653, which were dissolved in 0.5% methyl cellulose. CJ12567 was orally administered daily in a concentration of 30 mpk and 100 mpk and LY-2801653 in a concentration of 30 mpk for 14 days. During the administration, the tumor size was measured using a caliper at 3-day intervals and body weight of the mice were measured.

RON Gene Mutants

RON gene mutants (RON M1254T, RON R1335G, and RON R523Q) were used.

Example 1. Selection of RON Gene Variants From Tissues of Colon Cancer Patients

For confirming RON gene variants in the tissues of colon cancer patients, the present inventors have analyzed a total of 200 tissue samples of colon cancer patients.

First, for confirming the expression of RON wild-type or RONΔ155 or RONΔ160 variants in the colon cancer cell lines (HT29, colo320hsr, and MKN28) and the samples of colon cancer patients, RT-PCR was performed using the primers prepared by the present inventors.

As a result, as shown in FIG. 1a, it was confirmed that the HT29 cell line expressed the RONΔ160 variant while the colo320hsr cell line expressed the RONΔ155 variant. Additionally, it was confirmed that the RONΔ155 or RONΔ160 variant was expressed in sample Nos. 87 and 116 of colon cancer patients.

Then, for confirming the RON expression in the same samples as those of colon cancer patients in which RT-PCR was performed, western blot (FIG. 1b) and immunohistochemistry (FIG. 1c) were performed.

As a result, as shown in FIGS. 1b and 1c, the size of RON proteins in sample Nos. 87 and 116 of colon cancer patients, where the RONΔ155 variant or the RONΔ160 variant was confirmed, was the same as the protein size of the RONΔ160 variant in the HT29 cell line. Additionally, considering that the RONΔ160 variant can express the p-Tyr RON protein, it was confirmed that the RONΔ160 variant can activate RON proteins.

Example 2. Drug Sensitivity Analysis to CJ12567 in a RON Variant-Expressed Patient-Derived Colon Cancer Xenograft Model (PDX-Model)

For analyzing the drug sensitivity to CJ12567 in an in-vivo state, the present inventors transplanted sample Nos. 87 and 116 of colon cancer patients, which were determined to be positive to RON variants, into nude mice, and thereby a patient-derived colon cancer xenograft model (PDX-model) was prepared.

Meanwhile, during the process of preparing the xenograft model, as shown in FIG. 2b, when sample No. 116 of a colon cancer patient, which was determined to be positive to RON variants, was transplanted, the tumor tissue was much larger and more rapidly formed compared to that when sample No. 130, which was not determined to be positive to RON variants, was transplanted.

The mice in which the patient-derived colon cancer tissues were transplanted were administered with CJ12567 (30 mpk, 100 mpk), LY2801653 (30 mpk) as the positive control group, and vehicle (0.5% methyl cellulose) as the normal control group. Then, the size and weight of the cancer tissues were measured and subjected to IHC and western blotting analyses, thereby confirming the drug sensitivities.

2-1. Drug Sensitivity to CJ12567 in a Patient Sample No. 116-Derived Colon Cancer Xenograft Model (PDX-Model)

As shown in FIGS. 3a to 3c, when the patient-derived xenograft model (PDX-model), in which sample No. 116 of a colon cancer patient was transplanted into nude mice, was administered with CJ12567 (30 mpk), the size and weight of the cancer cells were significantly reduced by 53.15% and 47.87%, respectively, compared to those of the normal control group (the group administered with vehicle). Additionally, these values are similar to that of the positive control group, which was administered with LY2801653.

Additionally, when administered with CJ12567 (100 mpk), the size and weight of the cancer cells were considerably reduced by 35.05% and 18.09%, respectively, compared to those of the positive control group (the group administered with vehicle). These values represent the results that the size and weight of cancer cells were considerably reduced compared to that of the positive control group, which was administered with LY2801653 (FIGS. 3a to 3c).

Additionally, when administered with CJ12567 (100 mpk), there was no change in the amount of the total RON protein in both administrations of CJ12567 (100 mpk) and LY2801653 (30 mpk), as confirmed by immunohistochemistry method (FIG. 3d) and western blot (FIG. 3e). However, the expression of p-RON protein, which is active RON, was reduced and the expression of MSP and p-ERK proteins was also reduced, thus suggesting that the administration of CJ12567 (100 mpk) causes a decrease of MSP and p-ERK expression, thereby increasing the sensitivity.

2-2. Drug Sensitivity to CJ12567 in Patient Sample No. 87-Derived Colon Cancer Xenograft Model (PDX-Model)

As shown in FIGS. 3a to 3c, when the patient-derived xenograft model (PDX-model), in which sample No. 87 of a colon cancer patient was transplanted into nude mice, was administered with CJ12567 (30 mpk), the size and weight of the cancer cells were significantly reduced by 64.02% and 61.36%, respectively, compared to those of the normal control group (the group administered with vehicle). Additionally, these values are similar to that of the positive control group, which was administered with LY2801653.

Additionally, when administered with CJ12567 (100 mpk), the size and weight of the cancer cells were considerably reduced by 56.43% and 40.91%, respectively, compared to those of the positive control group (the group administered with vehicle). These values represent the results that the size and weight of cancer cells were considerably reduced compared to that of the positive control group, which was administered with LY2801653 (FIGS. 3a to 3c).

These results suggest the presence of a RON gene variant within the sample of a colon cancer patient increases the sensitivity to CJ12567.

Accordingly, the activated RON gene and RON gene variant show their potential use as a biomarker for predicting the sensitivity to CJ12567, which is a c-MET inhibitor.

Example 3. Drug Sensitivity Analysis to CJ12495 in a Wild-Type, a Mutant, and a Variant of RON Gene 3-1. Inhibition of RON Phosphorylation by CJ12495

The present inventors analyzed the inhibitory effect of CJ12495 treatment on RON phosphorylation in a wild-type, a mutant, and a variant of the RON gene.

First, the wild-type RON gene was overexpressed in a mouse embryonic fibroblast cell line (NIH3T3), activated by treating with MSP, and treated with CJ12495 in order to confirm the inhibition level against RON phosphorylation.

As a result, as shown in FIG. 4a, the western blot analysis using phospho-tyrosine antibody after immunoprecipitation with the RON protein confirmed that the RON gene was activated by MSP and that the phosphorylation of the activated RON was inhibited by the CJ12495 compound.

Additionally, each of the RON mutant genes (RON M1254T, RON R1335G, and RON R523Q) was overexpressed in a mouse embryonic fibroblast cell line, activated by treating with MSP, and treated with CJ12495 in order to confirm the inhibition level against RON phosphorylation.

As a result, as shown in FIG. 4b, the western blot analysis using phospho-tyrosine antibody after immunoprecipitation with the RON protein confirmed that the RON gene was activated by MSP and that the phosphorylation of the activated RON was inhibited in cells introduced with each of the RON mutant genes.

Additionally, each of the RON gene variants (RON-active Δ160 gene and RON-active Δ165 gene) was overexpressed in a mouse embryonic fibroblast cell line (NIH3T3) and treated with CJ12495 in order to confirm the inhibition level against RON phosphorylation.

As a result, as shown in FIG. 4c (RON-active Δ160 gene) and FIG. 4d (RON-active Δ165 gene), the western blot analysis using phospho-tyrosine antibody after immunoprecipitation with the RON protein confirmed that the phosphorylation of the active RON was inhibited in each of the groups treated with CJ12495.

From the above results, it was confirmed that the presence of a RON gene activated by MSP or an active RON gene can increase the sensitivity to CJ12495, thus enabling an excellent inhibitory effect of CJ12495 on RON phosphorylation.

3-2. Inhibitory Effect on Cell Motility Due to Inhibition of RON Phosphorylation by CJ12495

The present inventors analyzed the inhibitory effect on cell motility due to inhibition of RON phosphorylation caused by CJ12495 treatment in a wild-type, a mutant, and a variant of the RON gene.

First, the wild-type RON gene was overexpressed in a mouse embryonic fibroblast cell line (NIH3T3), activated by treating with MSP, and treated with CJ12495 in order to confirm cell motility.

As a result, as shown in FIG. 5a, the cell migration assay confirmed that the increased cell motility due to the activation by MSP was inhibited by CJ12495.

Additionally, each of the RON mutant genes (RON M1254T and RON R1335G) was overexpressed in a mouse embryonic fibroblast cell line, activated by treating with MSP, and treated with CJ12495 in order to confirm the cell motility.

As a result, as shown in FIG. 5b, the cell migration assay confirmed that the increased motility of the cells due to the activation by MSP was inhibited in both groups, where each group was introduced with each of the RON mutant genes and treated with CJ12495.

Additionally, each of the RON gene variants (RON-active Δ160 gene and RON-active Δ165 gene) was overexpressed in the mouse embryonic fibroblast cell line (NIH3T3) and treated with CJ12495 in order to confirm the inhibitory effect on cell motility.

As a result, as shown in FIG. 5c, the cell migration assay confirmed that the cell motility was inhibited in both groups treated with CJ12495.

From the above results, it was confirmed that the presence of a RON gene activated by MSP or an active RON gene increases the sensitivity to CJ12495, thus exhibiting an excellent inhibitory effect on cell motility by CJ12495.

3-3. Inhibitory Effect on Cell Metastasis Due to the Inhibition of RON Phosphorylation by CJ12495

The present inventors analyzed the inhibitory effect on cell metastasis due to inhibition of RON phosphorylation caused by CJ12495 treatment in a wild-type, a mutant, and a variant of the RON gene.

The wild-type RON gene and a mutant RON gene (R523Q) were each overexpressed in a mouse embryonic fibroblast cell line (NIH3T3), and RON was activated by treating with MSP and treated with CJ12495 in order to confirm the degree of cell invasion.

As a result, as shown in FIG. 6a, it was confirmed that the increased cell metastasis due to the activation by MSP was inhibited by CJ12495 treatment in both groups where each group was introduced with each of the wild-type RON gene and the R523Q mutant gene and treated with CJ12495.

Additionally, each of the RON mutant genes (RON M1254T and RON R1335G) was overexpressed in a mouse embryonic fibroblast cell line, activated by treating with MSP, and treated with CJ12495 in order to confirm the degree of cell invasion.

As a result, as shown in FIG. 6b, it was confirmed that the increased cell metastasis due to the activation by MSP was inhibited by CJ12495 treatment in both groups where each group was introduced with each of the RON gene mutant gene and treated with CJ12495.

Additionally, each of the RON mutant genes (RON-active Δ160 gene and RON-active Δ165 gene) was overexpressed in a mouse embryonic fibroblast cell line, activated by treating with MSP, and treated with CJ12495 in order to confirm the degree of cell invasion.

As a result, as shown in FIG. 6c, it was confirmed that the increased cell metastasis due to the activation by MSP was inhibited by CJ12495 treatment in both groups treated with CJ12495.

These results indicate that when RON is activated in cancer cells, for example, when a RON gene variant or a RON gene mutant is present, the sensitivity to CJ12495 can be increased.

Accordingly, active RON, e.g., a RON gene variant or RON gene mutant, shows its potential use as a biomarker for predicting the sensitivity to CJ12567.

Additionally, in the case when the active RON is expressed, CJ12495 may be used as an anticancer drug to the same.

Example 4. Drug Sensitivity Analysis to CJ12524 in a Wild-Type, a Mutant, and a Variant of RON Gene

4-1. Inhibition of RON Phosphorylation by CJ12524

The present inventors analyzed the inhibitory effect of CJ12524 treatment on RON phosphorylation in a wild-type, a mutant, and a variant of the RON gene.

HT29 and HCT8, colon cancer cell lines which have a high p-RON expression level because RON is always activated, were treated with CJ12524 in order to confirm the inhibition level against RON phosphorylation.

As a result, as shown in FIG. 7a, it was confirmed that RON phosphorylation was inhibited in the cells treated with various concentrations of CJ12524.

Additionally, Colo320HSR, a colon cancer cell line in which RON is not expressed, was introduced with the RON-active Δ155 gene and the RON-active Δ160 gene, which are constantly expressed in the Colo320HSR, and treated with CJ12524 in order to confirm the inhibitory effect against RON phosphorylation by CJ12524 treatment.

As a result, as shown in FIG. 7b, it was confirmed that RON phosphorylation was reduced when the cell lines were introduced with the RON-active Δ155 gene and the RON-active Δ160 gene and treated with CJ12524.

4-2. Induction of Apoptosis Due to Inhibition of RON Phosphorylation by CJ12524

The present inventors analyzed the effect of inducing apoptosis due to inhibition of RON phosphorylation by CJ12524 treatment.

HT29 and HCT8, the colon cancer cell lines which have a high p-RON expression level because RON is always phosphorylated, were treated with CJ12524 in order to confirm the presence of apoptosis.

As a result, as shown in FIG. 7c, it was confirmed that the CJ12524 treatment at various concentrations also increased the apoptosis according to the concentration. In particular, the RON phosphorylation was reduced and the expression of cleaved caspase 3 was increased.

Additionally, Colo320HSR, the colon cancer cell line in which RON is not expressed, was introduced with the RON-active Δ155 gene and the RON-active Δ160 gene, which are constantly active in the Colo320HSR, and treated with CJ12524 at various concentrations in order to confirm the presence of apoptosis.

As a result, as shown in FIG. 7d, it was confirmed that the CJ12524 treatment at various concentrations also increased the apoptosis according to the concentration. In particular, the RON phosphorylation was reduced and the expression of cleaved caspase 3, which is an apoptosis marker, was increased according to the concentration.

4-3. Inhibition of Cell Metastasis Due to Inhibition of RON Phosphorylation by CJ12524

The present inventors analyzed the effect of inhibiting cell metastasis due to inhibition of RON phosphorylation by CJ12524 treatment.

HCT8, a colon cancer cell line where RON is always phosphorylated, was treated with CJ12524 in order to confirm the degree of cell invasion.

As a result, as shown in FIG. 7e, it was confirmed that the CJ12524 treatment inhibited the degree of cell metastasis by about 60%.

Example 5. Drug Sensitivity Analysis to CJ12524 in a RON-Active Cancer Cell Xenograft Model (PDX-Model)

For analyzing the drug sensitivity to CJ12524 in an in-vivo state, the present inventors transplanted a cancer cell line which was determined to be positive against the RON activity into nude mice, and thereby a cancer cell-derived xenograft model (PDX-model) was prepared.

5-1. Confirmation of Tumor Inhibition by CJ12524 in an In-Vivo Xenograft Model The HCT8 cell line, where RON always shows an activity, was treated with CJ12524 at various concentrations for 14 days.

As a result, as shown in FIG. 8a, it was confirmed that when the tumor size was measured, the tumor growth was inhibited (top). In particular, there was almost no decrease in the body weight of the mice (bottom).

Additionally, as shown in FIG. 8b, when tumor tissue was ablated upon completion of drug administration and the tumor weight was measured, it was confirmed that the tumor weight was reduced in all groups treated with CJ12524.

5-2. Inhibition of RON Phosphorylation by CJ12524 in an In-Vivo Xenograft Model Upon completion of CJ12524 administration, the tissue was ablated and the presence of RON phosphorylation was confirmed.

As a result, based on the analyses by immunochemical staining method (FIG. 8c) and western blot (FIG. 8d), it was confirmed that the RON phosphorylation was decreased in the group treated with CJ12524.

These results indicate that when RON shows an activity in cancer cells, for example, when a RON gene variant or a RON gene mutant is present, the sensitivity to CJ12524 can be increased.

Accordingly, active RON, e.g., a RON gene variant or RON gene mutant, shows its potential use as a biomarker for predicting the sensitivity to CJ12524.

Additionally, in the case when the active RON is expressed, CJ12524 may be used as an anticancer drug for the same.

Example 6: Sensitivity Analysis to CJ12537 in a RON-Inactive Cancer Cell Xenograft Model

6-1. Confirmation of Tumor Inhibition by CJ12537 in an In-Vivo Xenograft Model It was confirmed whether tumor formation can be inhibited by CJ12537 in an animal model using the Colo320HSR cell line, where RON shows no activity.

Specifically, an animal model using the Colo320HSR cell line without RON activity (control group) and an animal model using the cell line introduced with the RON-active Δ155 gene and the RON-active Δ160 gene, which are constantly expressed, or a RON M1254T mutant were prepared, and their effects of inhibiting tumor formation by CJ12537 were compared.

As a result, as shown in Table 2 below, it was confirmed that CJ12537 treatment at various concentrations did not inhibit tumor formation at all in the control animal model without RON activity; however, CJ12537 treatment inhibited tumor formation in the RON-active variants.

TABLE 2

| Cell line | Construct | Inhibition of tumor growth (fold) | | |
|---|---|---|---|---|
| | | Vehicle | CJ 30 MPK | CJ 100 mpk |
| Colo320HSR (colon):pMET & pRON negative | control | 1 | 1 | 1 |
| | RON Δ160 | 1 | 0.71 | — |
| | RON Δ155 | 1 | 0.62 | 0.55 |
| | RON M1254T | 1 | 0.70 | 0.6 |

6-2. Confirmation of Tumor Inhibition by CJ12537 in a Stomach Cancer Cell Xenograft Model Without RON Activity It was confirmed whether tumor formation can be inhibited by CJ12537 in a stomach cancer xenograft mouse model without RON activity.

Specifically, 5-to 6-week-old Balb/c nude mice were subcutaneously injected with $1 \times 10^7$ cells (MKN1 parent, MKN1 RONΔ160 stable cell) and Matrigel at a 1:1 (v/v) ratio. When the tumor size grew to a size of 90 mm³ to 100 mm³, the mice were divided into groups and administered with drugs. Vehicle, CJ12537 (30 mpk), CJ12537 (100 mpk), and positive control (Amgen; 30 mpk) were orally administered daily. The tumor size was measured once in three days. Upon completion of the administration, the mice were sacrificed and tissues were ablated and the weight of tumor was measured. In particular, proteins were extracted from the tissues and the changes in expression pattern of p-RON and related proteins were confirmed by western blot analysis. Additionally, for confirming the change in tumor size, the tumor size was measured once every three days and compared and analyzed even after the completion of drug administration.

As a result, RON activation was not confirmed in the mouse model in which MKN1 cells were transplanted, and in the case without RON activity, there was no noticeable change in the tumor volume even when CJ12537 was administered (FIG. 9), thus confirming that there was no sensitivity to CJ12537.

From the above results, it was confirmed that in the case without RON activity, there is no sensitivity to CJ12537.

The invention claimed is:

1. A method for treating colon cancer in a human subject comprising:
  (a) measuring the expression level of an active form of RON(Recepteur d'Origine Nantais) within a biological sample obtained from the human subject with an agent selected from, an antisense oligonucleotide, a primer pair, or a probe which specifically binds to mRNA of the active RON or an antibody, a peptide, or a nucleotide that specifically binds to the active RON protein, wherein the active RON is at least one selected from the group consisting of a phosphorylated RON; α splicing variant which is RONΔ155 of SEQ ID NO: 1; α splicing variant which is RONΔ160 of SEQ ID NO: 2; α splicing variant which is RONΔ165 of SEQ ID NO: 3; a mutant in which the $1254^{th}$ amino acid in the polypeptide of SEQ ID NO: 4 is substituted from M to T; a mutant in which the $1335^{th}$ amino acid in the polypeptide of SEQ ID NO: 4 is substituted from R to G; a mutant in which the $523^{rd}$ amino acid in the polypeptide of SEQ ID NO: 4 is substituted from R to Q; a mutant in which the $1232^{nd}$ amino acid in the polypeptide of SEQ ID NO: 4 is substituted from D to V; and a mutant in which the $1268^{th}$ amino acid in the polypeptide of SEQ ID NO: 4 is substituted from M to T;
  (b) detecting increased expression of active RON in the biological sample as compared to a control level;
  (c) determining that the human subject is sensitive to a c-MET protein kinase inhibitor; and
  (d) administering the c-Met protein kinase inhibitor to the human subject who has been determined to be sensitive to the c-Met inhibitor
  wherein the protein kinase inhibitor is at least one selected from the group consisting of CJ12495, CJ12537, CJ12524, and CJ12567.

2. The method according to claim 1, wherein the primer pair consists of a forward primer of SEQ ID NO: 5 and a reverse primer of SEQ ID NO: 6.

3. The method according to claim 1, wherein an agent for measuring the expression level comprises an antibody capable of detecting the phosphorylation of RON.

* * * * *

SEQUENCE LISTING

```
<160> NUMBER OF SEQ ID NOS: 6

<210> SEQ ID NO 1
<211> LENGTH: 3732
<212> TYPE: DNA
<213> ORGANISM: Homo sapiens

<400> SEQUENCE: 1
atggagctcc tcccgccgct gcctcagtcc ttcctgttgc tgctgctgtt gcctgccaag       60
cccgcggcgg gcgaggactg gcagtgcccg cgcacccect acgcggcctc tcgcgacttt      120
gacgtgaagt acgtggtgcc cagcttctcc gccggaggcc tggtacaggc catggtgacc      180
tacgagggcg acagaaatga gagtgctgtg tttgtagcca tacgcaatcg cctgcatgtg      240
```

-continued

```
cttgggcctg acctgaagtc tgtccagagc ctggccacgg gccctgctgg agaccctggc    300
tgccagacgt gtgcagcctg tggcccagga ccccacggcc ctcccggtga cacagacaca    360
aaggtgctgg tgctggatcc cgcgctgcct gcgctggtca gttgtggctc cagcctgcag    420
ggccgctgct tcctgcatga cctagagccc caagggacag ccgtgcatct ggcagcgcca    480
gcctgcctct tctcagccca ccataaccgg cccgatgact gccccgactg tgtggccagc    540
ccattgggca cccgtgtaac tgtggttgag caaggccagg cctcctattt ctacgtggca    600
tcctcactgg acgcagccgt ggctgccagc ttcagcccac gctcagtgtc tatcaggcgt    660
ctcaaggctg acgcctcggg attcgcaccg ggctttgtgg cgttgtcagt gctgcccaag    720
catcttgtct cctacagtat tgaatacgtg cacagcttcc acacgggagc cttcgtgtac    780
ttcctgactg tacagccggc cagcgtgaca atgatcctag tgccctgca cacacgcctg    840 gcacggctta gcgccactga ccagagttg ggtgactatc gggagctggt cctcgactgc    900
agatttgctc caaaacgcag gcgccggggg gccccagaag gcggacagcc ctaccctgtg    960
ctgcgggtgg cccactccgc tccagtgggt gcccaacttg ccactgagct gagcatcgcc    1020
gagggccagg aagtactatt tggggtcttt gtgactggca aggatggtgg tcctggcgtg    1080
ggccccaact ctgtcgtctg tgccttcccc attgacctgc tggacacact aattgatgag    1140
ggtgtggagc gctgttgtga atccccagtc catccaggcc tccggcgagg cctcgacttc    1200
ttccagtcgc ccagttttg ccccaacccg cctggcctgg aagccctcag ccccaacacc    1260
agctgccgcc acttccctct gctggtcagt agcagcttct cacgtgtgga cctattcaat    1320
gggctgttgg gaccagtaca ggtcactgca ttgtatgtga cacgccttga caacgtcaca    1380
gtggcacaca tgggcacaat ggatgggcgt atcctgcagg tggagctggt caggtcacta    1440
aactacttgc tgtatgtgtc caacttctca ctgggtgaca gtgggcagcc cgtgcagcgg    1500
gatgtcagtc gtcttgggga ccacctactc tttgcctctg ggaccaggt tttccaggta    1560 cctatccaag gccctggctg ccgccacttc ctgacctgtg ggcgttgcct aagggcatgg    1620
catttcatgg gctgtggctg tgtgtgggaac atgtgcggcc agcagaagga gtgtcctggc    1680
tcctggcaac aggaccactg cccacctaag cttactgagg agccagtgct gatagcagtg    1740 caaccctct ttggcccacg ggcaggaggc acctgtctca ctcttgaagg ccagagtctg    1800
tctgtaggca ccagccgggc tgtgctggtc aatgggactg agtgtctgct agcacgggtc    1860 agtgagggc agcttttatg tgccacaccc cctggggcca cggtggccag tgtccccctt    1920
agcctgcagg tggggggtgc ccaggtacct ggttcctgga ccttccagta cagagaagac    1980
cctgtcgtgc taagcatcag ccccaactgt ggctacatca actcccacat caccatctgt    2040
ggccagcatc taacttcagc atggcactta gtgctgtcat tccatgacgg gcttagggca    2100
gtggaaagca ggcagtgtga gaggcagctt ccagagcagc agctgtgccg ccttcctgaa    2160
tatgtggtcc gagaccccca gggatgggtg gcagggaatc tgagtgcccg aggggatgga    2220
gctgctggct ttacactgcc tggctttcgc ttcctacccc caccccatcc acccagtgcc    2280
aacctagttc cactgaagcc tgaggagcat gccattaagt ttgaggtctg cgtagatggt    2340
gaatgtcata tcctgggtag agtggtgcgg ccagggccag atgggggtccc acagagcacg    2400 ctccttggta tcctgctgcc tttgctgctg cttgtggctg cactggcgac tgcactggtc    2460
ttcagctact ggtggcggag gaagcagcta gttcttcctc ccaacctgaa tgacctggca    2520 tccctgacc agactgctgg agccacaccc ctgcctattc tgtactcggg ctctgactac    2580
agaagtggcc ttgcactccc tgccattgat ggtctggatt ccaccacttg tgtccatgga    2640
```

```
gcatccttct ccgatagtga agatgaatcc tgtgtgccac tgctgcggaa agagtccatc    2700
cagctaaggg acctggactc tgcgctcttg gctgaggtca aggatgtgct gattccccat    2760
gagcgggtgg tcacccacag tgaccgagtc attggcaaag ccactttgg agttgtctac     2820 cacgagaat  acatagacca ggcccagaat cgaatccaat gtgccatcaa gtcactaagt    2880
cgcatcacag agatgcagca ggtggaggcc ttcctgcgag aggggctgct catgcgtggc    2940
ctgaaccacc cgaatgtgct ggctctcatt ggtatcatgt tgccacctga gggcctgccc    3000
catgtgctgc tgccctatat gtgccacggt gacctgctcc agttcatccg ctcacctcag    3060 cggaaccccca ccgtgaagga cctcatcagc tttggcctgc aggtagcccg cggcatggag   3120
tacctggcag agcagaagtt tgtgcacagg gacctggctg cgcggaactg catgctggac    3180
gagtcattca cagtcaaggt ggctgacttt ggtttggccc gcgacatcct ggacagggag    3240
tactatagtg ttcaacagca tcgccacgct cgcctacctg tgaagtggat ggcgctggag    3300
agcctgcaga cctatagatt taccaccaag tctgatgtgt ggtcatttgg tgtgctgctg    3360
tgggaactgc tgacacgggg tgccccacca taccgccaca ttgaccccttt tgaccttacc    3420 cacttcctgg cccagggtcg cgcctgcccc cagcctgagt attgccctga ttctctgtac    3480
caagtgatgc agcaatgctg ggaggcagac ccagcagtgc gacccacctt cagagtacta    3540 gtggggagg tggagcagat agtgtctgca ctgcttgggg accattatgt gcagctgcca    3600
gcaacctaca tgaacttggg ccccagcacc tcgcatgaga tgaatgtgcg tccagaacag    3660
ccgcagttct cacccatgcc agggaatgta cgccggcccc ggccactctc agagcctcct    3720
cggcccactt ga                                                       3732

<210> SEQ ID NO 2
<211> LENGTH: 3879
<212> TYPE: DNA
<213> ORGANISM: Homo sapiens

<400> SEQUENCE: 2
atggagctcc tcccgccgct gcctcagtcc ttcctgttgc tgctgctgtt gcctgccaag      60
cccgcggcgg gcgaggactg gcagtgcccg cgcacccct acgcggcctc tcgcgacttt     120
gacgtgaagt acgtggtgcc cagcttctcc gccggaggcc tggtacaggc catggtgacc     180
tacgagggcg acagaaatga gagtgctgtg tttgtagcca tacgcaatcg cctgcatgtg     240
cttgggcctg acctgaagtc tgtccagagc ctggccacgg gcctgctgg agaccctggc      300 tgccagacgt gtgcagcctg tgccccagga ccccacggcc ctcccggtga cacagacaca     360
aaggtgctgg tgctggatcc cgcgctgcct gcgctggtca gttgtggctc cagcctgcag     420
ggccgctgct cctgcatga  cctagagccc caagggacag ccgtgcatct ggcagcgcca     480
gcctgcctct tctcagccca ccataaccgg cccgatgact gccccgactg tgtggccagc     540
ccattgggca cccgtgtaac tgtggttgag caaggccagg cctcctattt ctacgtggca     600
tcctcactgg acgcagccgt ggctgccagc ttcagcccac gctcagtgtc tatcaggcgt     660
ctcaaggctg acgcctcggg attcgcaccg ggctttgtgg cgttgtcagt gctgcccaag     720
catcttgtct cctacagtat tgaatacgtg cacagcttcc acacgggagc cttcgtgtac     780
ttcctgactg tacagccggc cagcgtgaca gatgatccta gtgccctgca cacgcctcg     840 gcacggctta gcgccactga gccagagttg ggtgactatc gggagctggt cctcgactgc     900
agatttgctc caaaacgcag gcgccggggg gccccagaag gcggacagcc ctaccctgtg     960
```

```
ctgcgggtgg cccactccgc tccagtgggt gcccaacttg ccactgagct gagcatcgcc    1020
gagggccagg aagtactatt tggggtctit gtgactggca aggatggtgg tcctggcgtg    1080
ggccccaact ctgtcgtctg tgccttcccc attgacctgc tggacacact aattgatgag    1140
ggtgtggagc gctgttgtga atccccagtc catccaggcc tccggcgagg cctcgacttc    1200
ttccagtcgc ccagttttg ccccaacccg cctggcctgg aagccctcag ccccaacacc     1260
agctgccgcc acttccctct gctggtcagt agcagcttct cacgtgtgga cctattcaat    1320
gggctgttgg gaccagtaca ggtcactgca ttgtatgtga cacgccttga caacgtcaca    1380
gtggcacaca tgggcacaat ggatgggcgt atcctgcagg tggagctggt caggtcacta    1440
aactacttgc tgtatgtgtc caacttctca ctgggtgaca gtgggcagcc cgtgcagcgg    1500
gatgtcagtc gtcttgggga ccacctactc tttgcctctg ggaccaggt tttccaggta     1560 cctatccaag gccctggctg ccgccacttc ctgacctgtg ggcgttgcct aagggcatgg    1620
catttcatgg gctgtggctg tgtgtgggaac atgtgcggcc agcagaagga gtgtcctggc   1680
tcctggcaac aggaccactg cccacctaag cttactgagg agccagtgct gatagcagtg    1740
caacccctct ttggcccacg ggcaggaggc acctgtctca ctcttgaagg ccagagtctg    1800
tctgtaggca ccagccgggc tgtgctggtc aatgggactg agtgtctgct agcacgggtc    1860 agtgagggc agcttttatg tgccacaccc cctggggcca cggtggccag tgtccccctt     1920
agcctgcagg tgggggtgc ccaggtacct ggttcctgga ccttccagta cagagaagac     1980
cctgtcgtgc taagcatcag ccccaactgt ggctacatca actcccacat caccatctgt   2040
ggccagcatc taacttcagc atggcactta gtgctgtcat ccatgacgg gcttagggca    2100 gtggaaagca ggcagtgtga gaggcagctt ccagagcagc agctgtgccg ccttcctgaa   2160
tatgtggtcc gagaccccca gggatgggtg gcagggaatc tgagtgcccg aggggatgga   2220
gctgctggct ttacactgcc tggctttcgc ttcctacccc caccccatcc acccagtgcc   2280
aacctagttc cactgaagcc tgaggagcat gccattaagt ttgagtatat tgggctgggc   2340
gctgtggctg actgtgtggg tatcaacgtg accgtgggtg gtgagagctg ccagcacgag   2400
ttccgggggg acatggttgt ctgccccctg cccccatccc tgcagcttgg ccaggatggt   2460
gccccattgc aggtctgcgt agatggtgaa tgtcatatcc tgggtagagt ggtgcggcca   2520
gggccagatg gggtcccaca gagcacgctc cttggtatcc tgctgccttt gctgctgctt   2580
gtggctgcac tggcgactgc actggtcttc agctactggt ggcggaggaa gcagctagtt   2640
cttcctccca acctgaatga cctggcatcc ctggaccaga ctgctggagc cacacccctg   2700
cctattctgt actcgggctc tgactacaga agtggccttg cactccctgc cattgatggt   2760
ctggattcca ccacttgtgt ccatggagca tccttctccg atagtgaaga tgaatcctgt   2820
gtgccactgc tgcggaaaga gtccatccag ctaagggacc tggactctgc gctcttggct   2880
gaggtcaagg atgtgctgat tccccatgag cgggtggtca cccacagtga ccgagtcatt   2940
ggcaaaggcc actttggagt tgtctaccac ggagaatacc tagaccaggc ccagaatcga   3000
atccaatgtg ccatcaagtc actaagtcgc atcacagaga tgcagcaggt ggaggccttc   3060
ctgcgagagg ggctgctcat gcgtggcctg aaccacccga atgtgctggc tctcattggt   3120
atcatgttgc cacctgaggg cctgccccat gtgctgctgc cctatatgtg ccacggtgac   3180
ctgctccagt tcatccgctc acctcagcgg aaccccaccg tgaaggacct catcagcttt   3240
ggcctgcagg tagcccgcgg catggagtac ctggcagagc agaagtttgt gcacagggac   3300
ctggctgcgc ggaactgcat gctggacgag tcattcacag tcaaggtggc tgactttggt   3360
```

```
ttggcccgcg acatcctgga cagggagtac tatagtgttc aacagcatcg ccacgctcgc   3420
ctacctgtga agtggatggc gctggagagc ctgcagacct atagatttac caccaagtct   3480
gatgtgtggt catttggtgt gctgctgtgg gaactgctga cacggggtgc cccaccatac   3540
cgccacattg acccttttga ccttacccac ttcctggccc agggtcggcg cctgccccag   3600
cctgagtatt gccctgattc tctgtaccaa gtgatgcagc aatgctggga ggcagaccca   3660
gcagtgcgac ccaccttcag agtactagtg ggggaggtgg agcagatagt gtctgcactg   3720
cttggggacc attatgtgca gctgccagca acctacatga acttgggccc cagcacctcg   3780
catgagatga atgtgcgtcc agaacagccg cagttctcac ccatgccagg gaatgtacgc   3840
cggccccggc cactctcaga gcctcctcgg cccacttga                          3879

<210> SEQ ID NO 3
<211> LENGTH: 2460
<212> TYPE: DNA
<213> ORGANISM: Homo sapiens

<400> SEQUENCE: 3
atggagctcc tcccgccgct gcctcagtcc ttcctgttgc tgctgctgtt gcctgccaag     60
cccgcggcgg gcgaggactg gcagtgcccg cgcacccct acgcggcctc tcgcgacttt    120
gacgtgaagt acgtggtgcc cagcttctcc gccggaggcc tggtacaggc catggtgacc    180
tacgagggcg acagaaatga gagtgctgtg tttgtagcca tacgcaatcg cctgcatgtg    240
cttgggcctg acctgaagtc tgtccagagc ctggccacgg gccctgctgg agaccctggc    300
tgccagacgt gtgcagcctg tgcccagga ccccacggcc ctcccggtga cacagacaca     360
aaggtgctgg tgctggatcc cgcgctgcct gcgctggtca gttgtggctc cagcctgcag    420
ggccgctgct tcctgcatga cctagagccc caagggacag ccgtgcatct ggcagcgcca    480
gcctgcctct tctcagccca ccataaccgg cccgatgact gccccgactg tgtggccagc    540
ccattgggca cccgtgtaac tgtggttgag caaggccagg cctcctattt ctacgtggca    600
tcctcactgg acgcagccgt ggctgccagc ttcagcccac gctcagtgtc tatcaggcgt    660
ctcaaggctg acgcctcggg attcgcaccg ggctttgtgg cgttgtcagt gctgcccaag    720
catcttgtct cctacagtat tgaatacgtg cacagcttcc acacgggagc cttcgtgtac    780
ttcctgactg tacagccggc cagcgtgaca gatgatccta gtgccctgca cacgcctg      840 gcacggctta cgccactga gccagagttg ggtgactatc gggagctggt cctcgactgc    900
agatttgctc aaaacgcag gcgccggggg ccccagaag gcgacagcc ctaccctgtg       960 ctgcgggtgg cccactccgc tccagtgggt gcccaacttg ccactgagct gagcatcgcc   1020
gagggccagg aagtactatt tggggtctt gtgactggca aggatggtgg tcctggcgtg    1080
ggccccaact ctgtcgtctg tgccttcccc attgacctgc tggacacact aattgatgag   1140
ggtgtggagc gctgttgtga atccccagtc catccaggcc tccggcgagg cctcgacttc   1200
ttccagtcgc ccagttttg ccccaaccgc ctggcctgg aagccctcag ccccaacacc     1260
agctgccgcc acttccctct gctggtcagt agcagcttct cacgtgtgga cctattcaat   1320
gggctgttgg accagtacac ggtcactgca ttgtatgtga cacgccttga caacgtcaca   1380
gtggcacaca tgggcacaat ggatgggcgt atcctgcagg tggagctggt caggtcacta   1440
aactacttgc tgtatgtgtc caacttctca ctgggtgaca gtgggcagcc cgtgcagcgg   1500
gatgtcagtc gtcttgggga ccacctactc tttgcctctg ggaccaggt tttccaggta   1560
```

```
cctatccaag gccctggctg ccgccacttc ctgacctgtg ggcgttgcct aagggcatgg    1620
catttcatgg gctgtggctg gtgtgggaac atgtgcggcc agcagaagga gtgtcctggc    1680
tcctggcaac aggaccactg cccacctaag cttactgagg agccagtgct gatagcagtg    1740
caacccctct ttggcccacg ggcaggaggc acctgtctca ctcttgaagg ccagagtctg    1800
tctgtaggca ccagccgggc tgtgctggtc aatgggactg agtgtctgct agcacgggtc    1860
agtgaggggc agcttttatg tgccacaccc cctgggccca cggtggccag tgtcccccctt   1920 agcctgcagg tgggggtgc ccaggtacct ggttcctgga ccttccagta cagagaagac     1980
cctgtcgtgc taagcatcag ccccaactgt ggctacatca actcccacat caccatctgt    2040
ggccagcatc taacttcagc atggcactta gtgctgtcat ccatgacgg gcttagggca     2100 gtggaaagca gcagtgtga gaggcagctt ccagagcagc agctgtgccg ccttcctgaa     2160
tatgtggtcc gagaccccca gggatgggtg gcagggaatc tgagtgcccg aggggatgga    2220
gctgctggct ttacactgcc tggctttcgc ttcctacccc cacccccatcc acccagtgcc   2280 aacctagttc cactgaagcc tgaggagcat gccattaagt ttgaggtctg cgtagatggt    2340
gaatgtcata tcctgggtag agtggtgcgg ccagggccag atggggtccc acagagcacg    2400
ctccttggta tcctgctgcc tttgctgctg cttgtggctg cactggcgac tgcactggtc    2460
```

<210> SEQ ID NO 4
<211> LENGTH: 1400
<212> TYPE: PRT
<213> ORGANISM: Homo sapiens

<400> SEQUENCE: 4

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220
```

```
Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
            245                 250                 255

Ala Phe Val Tyr Phe Leu Thr Val Gln Pro Ala Ser Val Thr Asp Asp
        260                 265                 270

Pro Ser Ala Leu His Thr Arg Leu Ala Arg Leu Ser Ala Thr Glu Pro
    275                 280                 285

Glu Leu Gly Asp Tyr Arg Glu Leu Val Leu Asp Cys Arg Phe Ala Pro
290                 295                 300

Lys Arg Arg Arg Gly Ala Pro Glu Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640
```

-continued

Glu Leu Glu Pro Leu Gly Thr Gln Ala Val Gly Pro Thr Asn Val Ser
            645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
            675                 680                 685

Val Gln Pro Leu Phe Gly Pro Arg Ala Gly Gly Thr Cys Leu Thr Leu
            690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
            725                 730                 735

Ala Thr Pro Pro Gly Ala Thr Ala Ser Val Pro Leu Ser Leu Gln
            740                 745                 750

Val Gly Gly Ala Gln Val Pro Gly Ser Trp Thr Phe Gln Tyr Arg Glu
            755                 760                 765

Asp Pro Val Val Leu Ser Ile Ser Pro Asn Cys Gly Tyr Ile Asn Ser
            770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
            805                 810                 815

Gln Leu Pro Glu Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
            835                 840                 845

Ala Ala Gly Phe Thr Leu Pro Gly Phe Arg Phe Leu Pro Pro His
850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
            885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
            915                 920                 925

Ala Pro Leu Gln Val Cys Val Asp Gly Glu Cys His Ile Leu Gly Arg
            930                 935                 940

Val Val Arg Pro Gly Pro Asp Gly Val Pro Gln Ser Thr Leu Leu Gly
945                 950                 955                 960

Ile Leu Leu Pro Leu Leu Leu Leu Val Ala Ala Leu Ala Thr Ala Leu
            965                 970                 975

Val Phe Ser Tyr Trp Trp Arg Arg Lys Gln Leu Val Leu Pro Pro Asn
            980                 985                 990

Leu Asn Asp Leu Ala Ser Leu Asp Gln Thr Ala Gly Ala Thr Pro Leu
            995                 1000                1005

Pro Ile Leu Tyr Ser Gly Ser Asp Tyr Arg Ser Gly Leu Ala Leu
            1010                1015                1020

Pro Ala Ile Asp Gly Leu Asp Ser Thr Thr Cys Val His Gly Ala
            1025                1030                1035

Ser Phe Ser Asp Ser Glu Asp Glu Ser Cys Val Pro Leu Leu Arg
            1040                1045                1050

Lys Glu Ser Ile Gln Leu Arg Asp Leu Asp Ser Ala Leu Leu Ala

```
            1055                1060                1065

Glu Val Lys Asp Val Leu Ile Pro His Glu Arg Val Val Thr His
        1070                1075                1080

Ser Asp Arg Val Ile Gly Lys Gly His Phe Gly Val Val Tyr His
        1085                1090                1095

Gly Glu Tyr Ile Asp Gln Ala Gln Asn Arg Ile Gln Cys Ala Ile
        1100                1105                1110

Lys Ser Leu Ser Arg Ile Thr Glu Met Gln Gln Val Glu Ala Phe
        1115                1120                1125

Leu Arg Glu Gly Leu Leu Met Arg Gly Leu Asn His Pro Asn Val
        1130                1135                1140

Leu Ala Leu Ile Gly Ile Met Leu Pro Pro Glu Gly Leu Pro His
        1145                1150                1155

Val Leu Leu Pro Tyr Met Cys His Gly Asp Leu Leu Gln Phe Ile
        1160                1165                1170

Arg Ser Pro Gln Arg Asn Pro Thr Val Lys Asp Leu Ile Ser Phe
        1175                1180                1185

Gly Leu Gln Val Ala Arg Gly Met Glu Tyr Leu Ala Glu Gln Lys
        1190                1195                1200

Phe Val His Arg Asp Leu Ala Ala Arg Asn Cys Met Leu Asp Glu
        1205                1210                1215

Ser Phe Thr Val Lys Val Ala Asp Phe Gly Leu Ala Arg Asp Ile
        1220                1225                1230

Leu Asp Arg Glu Tyr Tyr Ser Val Gln Gln His Arg His Ala Arg
        1235                1240                1245

Leu Pro Val Lys Trp Met Ala Leu Glu Ser Leu Gln Thr Tyr Arg
        1250                1255                1260

Phe Thr Thr Lys Ser Asp Val Trp Ser Phe Gly Val Leu Leu Trp
        1265                1270                1275

Glu Leu Leu Thr Arg Gly Ala Pro Pro Tyr Arg His Ile Asp Pro
        1280                1285                1290

Phe Asp Leu Thr His Phe Leu Ala Gln Gly Arg Arg Leu Pro Gln
        1295                1300                1305

Pro Glu Tyr Cys Pro Asp Ser Leu Tyr Gln Val Met Gln Gln Cys
        1310                1315                1320

Trp Glu Ala Asp Pro Ala Val Arg Pro Thr Phe Arg Val Leu Val
        1325                1330                1335

Gly Glu Val Glu Gln Ile Val Ser Ala Leu Leu Gly Asp His Tyr
        1340                1345                1350

Val Gln Leu Pro Ala Thr Tyr Met Asn Leu Gly Pro Ser Thr Ser
        1355                1360                1365

His Glu Met Asn Val Arg Pro Glu Gln Pro Gln Phe Ser Pro Met
        1370                1375                1380

Pro Gly Asn Val Arg Arg Pro Arg Pro Leu Ser Glu Pro Pro Arg
        1385                1390                1395

Pro Thr
        1400

<210> SEQ ID NO 5
<211> LENGTH: 20
<212> TYPE: DNA
<213> ORGANISM: Artificial Sequence
<220> FEATURE:
<223> OTHER INFORMATION: RON forward primer
```

```
<400> SEQUENCE: 5
ctctggggac caggttttcc                                            20

<210> SEQ ID NO 6
<211> LENGTH: 20
<212> TYPE: DNA
<213> ORGANISM: Artificial Sequence
<220> FEATURE:
<223> OTHER INFORMATION: RON reverse primer

<400> SEQUENCE: 6
accatcaatg gcagggagtg                                            20
```